United States Patent
Chun et al.

(10) Patent No.: US 10,689,482 B2
(45) Date of Patent: Jun. 23, 2020

(54) EPOXY COMPOUND HAVING ALKOXYSILYL GROUP, COMPOSITION AND HARDENED MATERIAL COMPRISING SAME, USE FOR SAME, AND PRODUCTION METHOD FOR EPOXY COMPOUND HAVING ALKOXYSILYL GROUP

(71) Applicant: KOREA INSTITUTE OF INDUSTRIAL TECHNOLOGY, Cheonan (KR)

(72) Inventors: Hyun-Aee Chun, Seongnam (KR); Su-Jin Park, Ansan (KR); Sang-Yong Tak, Busan (KR); Yun-Ju Kim, Seoul (KR); Sook-Yeon Park, Gunpo (KR); Sung-Hwan Park, Gunpo (KR)

(73) Assignee: KOREA INSTITUTE OF INDUSTRIAL TECHNOLOGY, Cheonan (KR)

( * ) Notice: Subject to any disclaimer, the term of this patent is extended or adjusted under 35 U.S.C. 154(b) by 789 days.

(21) Appl. No.: 14/390,340

(22) PCT Filed: Apr. 2, 2013

(86) PCT No.: PCT/KR2013/002730
§ 371 (c)(1),
(2) Date: Oct. 2, 2014

(87) PCT Pub. No.: WO2013/151308
PCT Pub. Date: Oct. 10, 2013

(65) Prior Publication Data
US 2015/0051316 A1    Feb. 19, 2015

(30) Foreign Application Priority Data

Apr. 2, 2012 (KR) .......................... 10-2012-0034070
Apr. 2, 2013 (KR) .......................... 10-2013-0035546

(51) Int. Cl.
*C08G 59/30* (2006.01)
*C08G 59/32* (2006.01)
(Continued)

(52) U.S. Cl.
CPC ......... *C08G 59/306* (2013.01); *C07D 303/26* (2013.01); *C07D 303/28* (2013.01);
(Continued)

(58) Field of Classification Search
None
See application file for complete search history.

(56) References Cited

U.S. PATENT DOCUMENTS 3,935,346 A * 1/1976 Stengle .................. C08J 7/047
                                                      427/387
4,220,513 A    9/1980 Green et al.
(Continued)

FOREIGN PATENT DOCUMENTS

CN   1293685 A    5/2001
CN   1303382 A    7/2001
(Continued)

OTHER PUBLICATIONS

Chinese Office Action for Chinese Patent Application No. 201280052291.8 dated Oct. 28, 2015.
(Continued)

*Primary Examiner* — Randy P Gulakowski
*Assistant Examiner* — Ha S Nguyen

(57) ABSTRACT

The present invention relates to an alkoxysilylated epoxy compound, a composite exhibiting good heat resistance properties, low CTE and high glass transition temperature and not requiring a coupling agent, a composition including the same, a cured product formed of the composition, a use of the cured product, and a method of preparing the epoxy compound having alkoxysilyl group. An epoxy compound
(Continued)

having an epoxy group and an alkoxysilyl group, a composition including the epoxy compound, a curing agent, a filler and/or a reaction catalyst, a cured product of the composition, and a use of the composition including an electronic part are provided. In a composite and/or cured product, the epoxy composition exhibits improved heat resistance properties, decreased CTE, and increased glass transition temperature or Tg-less. The cured product exhibits good flame retardant properties by the introduction of the alkoxysilyl group.

9 Claims, 3 Drawing Sheets

(51) Int. Cl.
| | |
|---|---|
| C07D 303/38 | (2006.01) |
| C08G 59/22 | (2006.01) |
| C08K 7/14 | (2006.01) |
| C08G 59/38 | (2006.01) |
| C07F 7/18 | (2006.01) |
| C07D 303/26 | (2006.01) |
| C08L 63/00 | (2006.01) |
| C07D 303/28 | (2006.01) |

(52) U.S. Cl.
CPC ............ C07F 7/1804 (2013.01); C08G 59/22 (2013.01); C08G 59/3281 (2013.01); C08G 59/38 (2013.01); C08K 7/14 (2013.01); C08L 63/00 (2013.01)

(56) References Cited

U.S. PATENT DOCUMENTS

| | | | |
|---|---|---|---|
| 4,292,151 A | 9/1981 | Inata et al. | |
| 4,789,711 A | 12/1988 | Monnier et al. | |
| 5,019,607 A * | 5/1991 | Coltrain ................. | C08G 18/58 523/435 |
| 5,248,710 A | 9/1993 | Shiobara et al. | |
| 5,300,588 A | 4/1994 | Shiobara et al. | |
| 5,336,786 A | 8/1994 | Shiobara et al. | |
| 6,087,513 A | 7/2000 | Liao et al. | |
| 7,408,015 B2 | 8/2008 | Kang et al. | |
| 2003/0078322 A1 | 4/2003 | Honda et al. | |
| 2004/0241331 A1 | 12/2004 | Durairaj et al. | |
| 2007/0100043 A1 | 5/2007 | Shiono | |
| 2007/0282081 A1 | 12/2007 | Ichiroku | |
| 2008/0221238 A1 | 9/2008 | Su et al. | |
| 2011/0082321 A1 | 4/2011 | Sakurai et al. | |
| 2011/0143092 A1 | 6/2011 | Asai et al. | |
| 2011/0194261 A1* | 8/2011 | Tanaka .................... | B32B 17/04 361/748 |
| 2011/0319589 A1 | 12/2011 | Takeyama et al. | |
| 2012/0041102 A1 | 2/2012 | Chun et al. | |
| 2012/0153512 A1 | 6/2012 | Sugimoto et al. | |
| 2012/0292487 A1 | 11/2012 | Yukawa et al. | |
| 2012/0295199 A1 | 11/2012 | Takeyama et al. | |
| 2012/0315765 A1 | 12/2012 | Nakajima et al. | |

FOREIGN PATENT DOCUMENTS

| | | |
|---|---|---|
| CN | 1784462 A | 6/2006 |
| CN | 101701058 A | 5/2010 |
| EP | 0 618 246 A2 | 10/1994 |
| EP | 1114834 A1 | 11/2001 |
| EP | 2 119 721 A1 | 11/2009 |
| EP | 2 767 535 A2 | 8/2014 |
| JP | 61-272244 A | 12/1986 |
| JP | 62-050312 A | 3/1987 |
| JP | S62-292828 A | 12/1987 |
| JP | S63-280720 A | 11/1988 |
| JP | 06-345847 A | 12/1994 |
| JP | 07-258240 A | 10/1995 |
| JP | 08-193091 A | 7/1996 |
| JP | 2003-055435 A | 2/2003 |
| JP | 2003-141933 A | 5/2003 |
| JP | 2006-012784 A | 1/2006 |
| JP | 2006-137800 A | 6/2006 |
| JP | 2007-126496 A | 5/2007 |
| JP | 2010-003897 A | 1/2010 |
| JP | 2010-065161 A | 3/2010 |
| JP | 2010-520952 A | 6/2010 |
| JP | 2011-057755 A | 3/2011 |
| JP | 2011-208120 A | 10/2011 |
| JP | 2012-246422 A | 12/2012 |
| JP | 2012-246425 A | 12/2012 |
| KR | 10-0929380 B1 | 12/2009 |
| WO | WO 99/62894 A2 | 12/1999 |
| WO | WO 2010/092947 A1 | 8/2010 |
| WO | WO 2011/093188 A1 | 8/2011 |
| WO | WO 2011/093236 A1 | 8/2011 |
| WO | WO 2011/102470 A1 | 8/2011 |
| WO | WO 2011/142468 A1 | 11/2011 |
| WO | WO 2012/070637 A1 | 5/2012 |
| WO | WO 2013/180375 A1 | 12/2013 |

OTHER PUBLICATIONS

Chinese Office Action for Chinese Patent Application No. 201380046568.0 dated Nov. 2, 2015.
Extended European Search Report for European Patent Application No. 13772355.7 dated Oct. 16, 2015.
Extended European Search Report for European Patent Application No. 13796871.5 dated Dec. 9, 2015.
Tahseen Razzaq et al., "Investigating the Existence of Nonthermal/Specific Microwave Effects Using Silicon Carbide Heating Elements as Power Modulators", The Journal of Organic Chemistry, 2008, pp. 6321-6329, vol. 73, No. 16, American Chemical Society.
International Search Report for PCT/KR2013/002730 filed on Apr. 2, 2013.
Chinese Office Action for CN Application No. 201280053687.4, dated May 20, 2015.
Nobuo Suzuki et al., "Concise Encyclopedia of Polymer Science and Engineering", Polymer Dictionary, 1994, pp. 455-456, Maruzen Inc., Japan.
Extended European Search Report for European Application No. 13813009.1 dated Feb. 12, 2016.
Tsung-Han Ho et al., "Modification of epoxy resin with siloxane containing phenol aralkyl epoxy resin for electronic encapsulation application" European Polymer Journal, 2001, pp. 267-274, vol. 37, Elsevier Science Ltd.
Barry Arkles, "Silane Coupling Agents: Connecting Across Boundaries", 2006, pp. 1-60, Gelest Inc., http://www.gelest.de/goods/pdf/couplingagents.pdf.
Zhang et al., "Characterization of siliconized diallyl bisphenol A type epoxy resin and study on its curing properties", Chemistry and Adhesion, Jun. 28, 2006, pp. 369-371 & 375, vol. 28, No. 6, Huaxue Yu Nianhe Bianji Weiyuanhui.
Lei Xue et al., "Precise Synthesis of Poly(silphenylenesiloxane)s with Epoxy Side Functional Groups by Tris(pentafluorophenyl)borane as a Catalyst", Polymer Journal, Mar. 5, 2007, pp. 379-388, vol. 39, No. 4, The Society of Polymer Science, Japan.
Office Action from U.S. Appl. No. 14/404,942 dated Jul. 19, 2017.

* cited by examiner

[Figure 1]
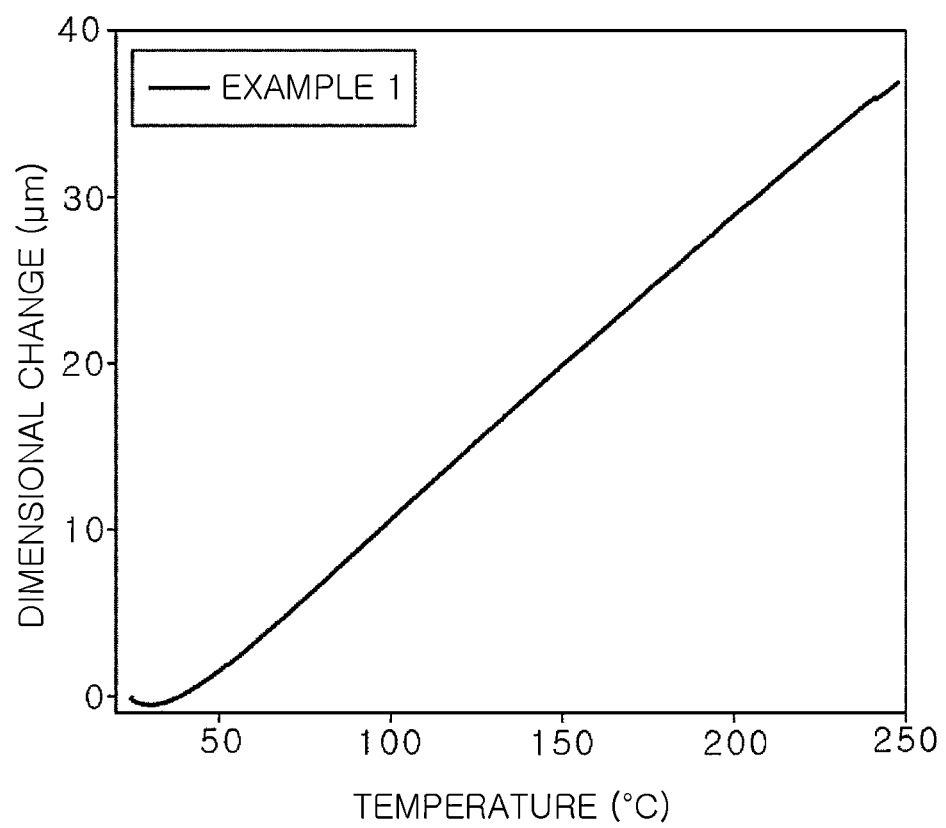

[Figure 2]
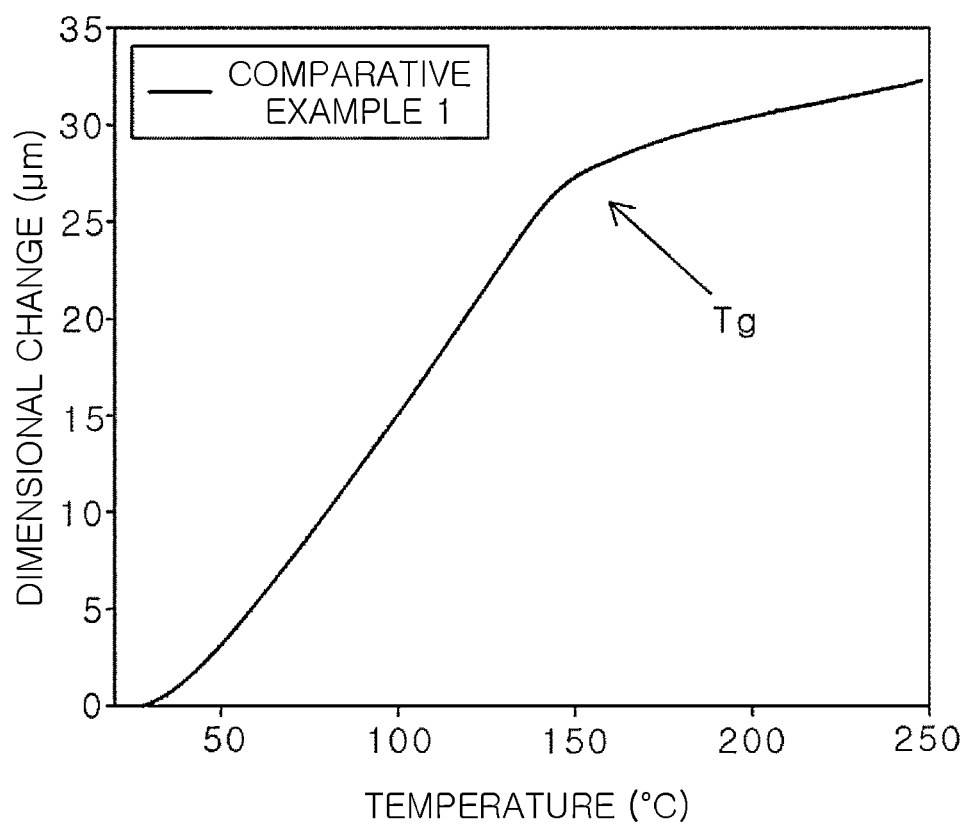

【Figure 3】
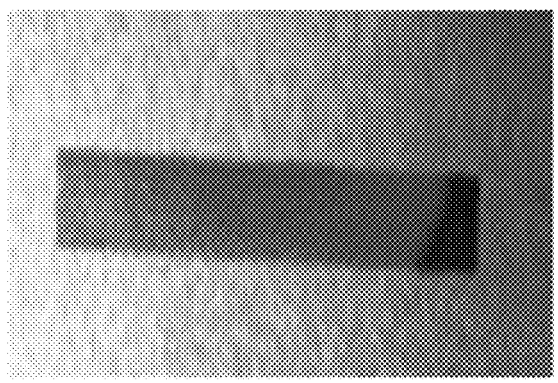  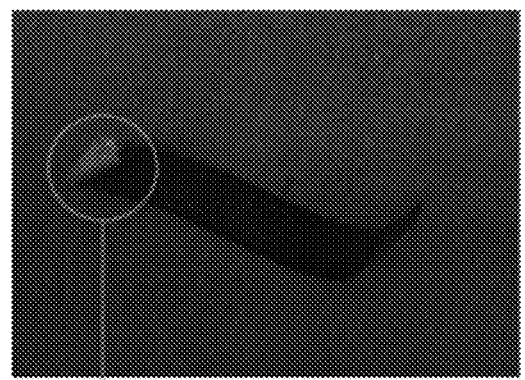
EXAMPLE 1   COMPARATIVE EXAMPLE 1
HOLD PART WITH TWEEZERS

EPOXY COMPOUND HAVING ALKOXYSILYL GROUP, COMPOSITION AND HARDENED MATERIAL COMPRISING SAME, USE FOR SAME, AND PRODUCTION METHOD FOR EPOXY COMPOUND HAVING ALKOXYSILYL GROUP

TECHNICAL FIELD

The present invention relates to an epoxy compound having an alkoxysilyl group (hereinafter 'alkoxysilylated epoxy compound') exhibiting good heat resistance properties, a composition including the same, a cured product formed of the composition, a use of the cured product, and a method of preparing the epoxy compound having an alkoxysilyl group. More particularly, the present invention relates to an alkoxysilylated epoxy compound, a composite of which exhibits good heat resistance properties, in particular, exhibiting a low coefficient of thermal expansion (CTE) and a high increasing effect of glass transition temperature (including a transition temperature-less (Tg-less) compound, not having a glass transition temperature) and not requiring a coupling agent, a composition including the same, a cured product formed of the composition, a use of the cured product, and a method of preparing the epoxy compound having an alkoxysilyl group.

BACKGROUND ART

The coefficient of thermal expansion (CTE) of a polymer material—specifically, a cured product formed of an epoxy compound—is about 50 to 80 ppm/° C., a significantly high level, on the level of several to ten times the CTE of a inorganic material such as ceramic material or a metal (for example, the CTE of silicon is 3 to 5 ppm/° C., and the CTE of copper is 17 ppm/° C.). Thus, when the polymer material is used in conjunction with the inorganic material or the metal in a semiconductor, a display, or the like, the properties and processability of the polymer material are significantly limited due to the different CTEs of the polymer material and the inorganic material or the metal. In addition, during semiconductor packaging in which a silicon wafer and a polymer substrate are used side by side, or during a coating process in which a polymer film is coated with an inorganic shielding layer to impart gas barrier properties, product defects such as the generation of cracks in an inorganic layer, the warpage of a substrate, the peeling-off of a coating layer, the failure of a substrate, and the like, may be generated due to a large CTE-mismatch between constituent elements due to changes in processing and/or applied temperature conditions.

Because of the high CTE of the polymer material and the resultant dimensional change of the polymer material, the development of technologies such as next generation semiconductor substrates, printed circuit boards (PCBs), packaging, organic thin film transistors (OTFTs), and flexible display substrates may be limited. Particularly, at the current time, in the semiconductor and PCB fields, designers are facing challenges in the design of next generation parts requiring high degrees of integration, miniaturization, flexibility, performance, and the like, in securing processability and reliability in parts due to polymer materials having significantly high CTE as compared to metal/ceramic materials. In other words, due to the high thermal expansion properties of the polymer material at part processing temperatures, defects may be generated, processability may be limited, and the design of the parts and the securing of processability and reliability therein may be objects of concern. Accordingly, improved thermal expansion properties or dimensional stability of the polymer material are necessary in order to secure processability and reliability in electronic parts.

In general, in order to improve thermal expansion properties—i.e., to obtain a low CTE in a polymer material such as an epoxy compound, (1) a method of producing a composite of the epoxy compound with inorganic particles (an inorganic filler) and/or fibers and (2) a method of designing a novel epoxy compound having a decreased CTE have been used.

When the composite of the epoxy compound and the inorganic particles as the filler are formed in order to improve thermal expansion properties, a large amount of silica inorganic particles, having about 2 to 30 μm is required to be used to obtain a CTE decrease effect. However, due to the presence of the large amount of inorganic particles, the processability and physical properties of the parts may be deteriorated. That is, the presence of the large amount of inorganic particles may decrease fluidity, and voids may be generated during the filling of narrow spaces. In addition, the viscosity of the material may increase exponentially due to the addition of the inorganic particles. Further, the size of the inorganic particles tends to decrease due to semiconductor structure miniaturization. When a filler having a particle size of 1 μm or less is used, the decrease in fluidity (viscosity reduction) may be worsened. When inorganic particles having a large average particle diameter are used, the frequency of insufficient filling in the case of a composition including a resin and the inorganic particles may increase. While the CTE may largely decrease when a composition including an organic resin and a fiber as the filler is used, the CTE may remain high as compared to that of a silicon chip or the like.

As described above, the manufacturing of highly integrated and high performance electronic parts for next generation semiconductor substrates, PCBs, and the like may be limited due to the limitations in the technology of the combination of epoxy compounds. Thus, the development of a polymer composite having improved heat resistance properties—namely, a low CTE and a high glass transition temperature—is required to overcome the challenge of a lack of heat resistance properties due to a high CTE and processability of a common thermosetting polymer composite.

DISCLOSURE

Technical Problem

An embodiment of the present invention provides an alkoxysilylated epoxy compound, a composite of which exhibits good heat resistance properties, particularly low CTE and high glass transition temperature properties and a cured product exhibiting good flame retardant property.

Another embodiment of the present invention provides an epoxy composition, a composite of which exhibits good heat resistance properties, particularly low CTE and high glass transition temperature properties and a cured product exhibiting good flame retardant property.

Further another embodiment of the present invention provides a cured product of an epoxy composition in accordance with an exemplary embodiment, a composite of which exhibits good heat resistance properties, particularly low CTE and high glass transition temperature properties, while the cured product exhibits good flame retardant property.

In addition, another embodiment of the present invention provides a use of an epoxy composition in accordance with an exemplary embodiment.

Another embodiment of the present invention provides a method of preparing an epoxy compound having an alkoxysilyl group.

Technical Solution

According to the first embodiment of the present invention, there is provided an epoxy compound having an alkoxysilyl group having a structure of the following Formula 1.

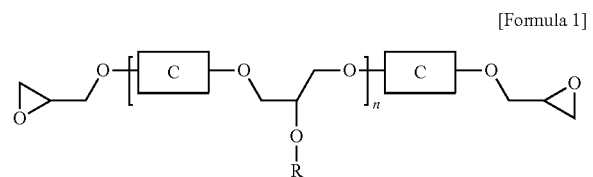

[Formula 1]

In Formula 1, a core unit C is independently selected from structures of the following Formulae 2-1 to 2-5, and each core unit C of a plurality of the core units C present in the above Formula 1 may be the same or different.

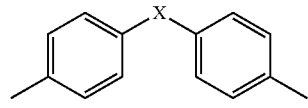

[Formula 2-1]

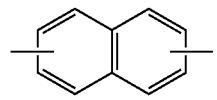

[Formula 2-2]

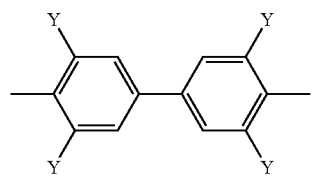

[Formula 2-3]

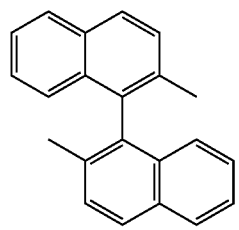

[Formula 2-4]

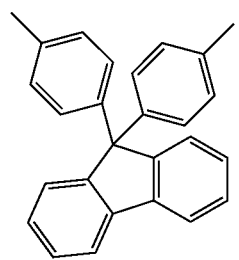

[Formula 2-5]

In Formula 2-1, X is —$CH_2$—, —$C(CH_3)_2$—, —$C(CF_3)_2$—, —S— or —$SO_2$—.

In Formula 2-3, Y is independently selected from the group consisting of H and an alkyl group of C1 to C5.

Here, n is an integer from 1 to 10, in the case that n is 1, R has a structure of the following Formula 3a or 3b, in the case that n is at least 2, at least one R of a plurality of R has a structure of the following Formula 3a or 3b, and the remainder thereof are hydrogen atoms, and an epoxy compound containing all core units having the above Formula 2-1 in which X is —$C(CH_3)_2$—, and R has the following Formula 3b is excluded from the epoxy compound of the above Formula 1.

—$(CH_2)_m$—$SiR_aR_bR_c$   [Formula 3a]

—$CONH(CH_2)_m$—$SiR_aR_bR_c$   [Formula 3b]

In Formulae 3a and 3b, at least one of $R_a$ to $R_c$ is an alkoxy group having 1 to 5 carbon atoms, and the remainder thereof are alkyl groups having 1 to 10 carbon atoms, the alkoxy group and the alkyl group may be a linear chain or a branched chain alkoxy group or alkyl group, and m is an integer from 3 to 10.

According to the second embodiment of the present invention, there is provided an epoxy composition including an epoxy compound having an alkoxysilyl group and a structure of the following Formula 1.

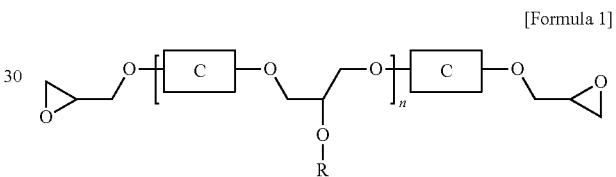

[Formula 1]

In Formula 1, a core unit C is independently selected from structures of the following Formulae 2-1 to 2-5, and each core unit C of a plurality of the core units C present in the above Formula 1 may be the same or different.

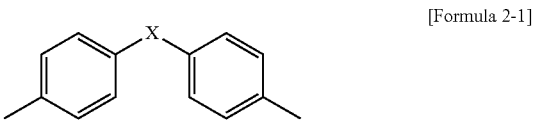

[Formula 2-1]

[Formula 2-2]

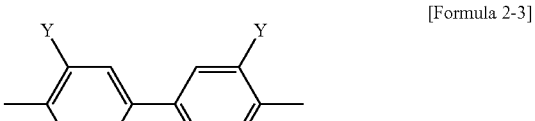

[Formula 2-3]

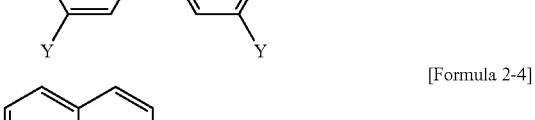

[Formula 2-4]

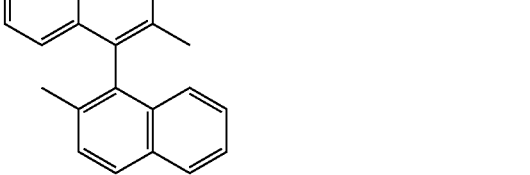

-continued

[Formula 2-5]

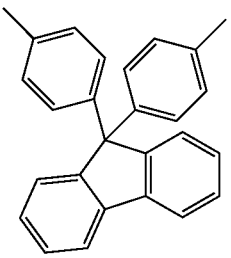

In Formula 2-1, X is —CH$_2$—, —C(CH$_3$)$_2$—, —C(CF$_3$)$_2$—, —S— or —SO$_2$—.

In Formula 2-3, Y is independently selected from the group consisting of H and an alkyl group of C1 to C5.

Here, n is an integer from 1 to 10, in the case that n is 1, R has a structure of the following Formula 3a or 3b, and in the case that n is at least 2, at least one R of a plurality of R has a structure of the following Formula 3a or 3b, and the remainder thereof are hydrogen atoms.

[Formula 3a]

[Formula 3b]

In Formulae 3a and 3b, at least one of R$_a$ to R$_c$ is an alkoxy group having 1 to 5 carbon atoms, and the remainder thereof are alkyl groups having 1 to 10 carbon atoms, the alkoxy group and the alkyl group may be a linear chain or a branched chain alkoxy group or alkyl group, and m is an integer from 3 to 10.

According to the third embodiment of the present invention, the epoxy composition of the second embodiment, in which, at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound is further included, may be provided.

According to the fourth embodiment of the present invention, the epoxy composition of the second embodiment, in which the epoxy compound includes bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolak unit, as a core structure, may be provided.

According to the fifth embodiment of the present invention, the epoxy composition of the fourth embodiment, in which the epoxy compound includes the bisphenol A, the biphenyl, the naphthalene, or the fluorene as the core structure, may be provided.

According to the sixth embodiment of the present invention, the epoxy composition of the third embodiment, in which the epoxy composition includes 10 wt % to 100 wt % of the epoxy compound having an alkoxysilyl group and 0 wt % to 90 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on the total amount of the epoxy compound, may be provided.

According to the seventh embodiment of the present invention, the epoxy composition of the sixth embodiment, in which the epoxy composition includes 30 wt % to 100 wt % of the epoxy compound having an alkoxysilyl group and 0 wt % to 70 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on the total amount of the epoxy compound, may be provided.

According to the eighth embodiment of the present invention, the epoxy composition according to any one of the second to seventh embodiments, in which at least one kind of filler selected from the group consisting of inorganic particles and a fiber is included, may be provided.

According to the ninth embodiment of the present invention, the epoxy composition of the eighth embodiment, in which the inorganic particle is at least one selected from the group consisting of a metal oxide selected from the group consisting of silica, zirconia, titania, alumina, silicon nitride and aluminum nitride, T-10 type silsesquioxane, ladder type silsesquioxane and cage type silsesquioxane, may be provided.

According to a tenth embodiment of the present invention, the epoxy composition of the eighth embodiment, in which an amount of the inorganic particles is 5 wt % to 95 wt % based on a total solid content of the epoxy composition, may be provided.

According to the eleventh embodiment of the present invention, the epoxy composition of the tenth embodiment, in which an amount of the inorganic particles is 30 wt % to 95 wt % based on a total solid content of the epoxy composition, may be provided.

According to the twelfth embodiment of the present invention, the epoxy composition of the tenth embodiment, in which an amount of the inorganic particles is 5 wt % to 60 wt % based on a total solid content of the epoxy composition, may be provided.

According to the thirteenth embodiment of the present invention, the epoxy composition of the eighth embodiment, in which the fiber is at least one selected from the group consisting of a glass fiber selected from the group consisting of an E-glass fiber, a T-glass fiber, an S-glass fiber, an NE-glass fiber, an E-glass fiber, a H-glass fiber and quartz, and an organic fiber selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber, may be provided.

According to the fourteenth embodiment of the present invention, the epoxy composition of the thirteenth embodiment, in which the fiber is the E-glass fiber, may be provided.

According to the fifteenth embodiment of the present invention, the epoxy composition of the thirteenth embodiment, in which the fiber is the T-glass fiber, may be provided.

According to the sixteenth embodiment of the present invention, the epoxy composition of the eighth embodiment, in which an fiber content is 10 wt % to 90 wt % based on a total solid content of the epoxy composition, may be provided.

According to the seventeenth embodiment of the present invention, the epoxy composition of the eighth embodiment, in which the inorganic particles are further included in the case that the fiber is included therein, may be provided.

According to the eighteenth embodiment of the present invention, the epoxy composition according to any one of the second to seventeenth embodiments, in which a curing agent is further included, may be provided.

According to the nineteenth embodiment of the present invention, the epoxy composition according to any one of the second to eighteenth embodiments, in which an reaction catalyst for alkoxysilyl group is further included, may be provided.

According to the twentieth embodiment of the present invention, the epoxy composition of the nineteenth embodiment, in which the reaction catalyst for alkoxysilyl group is at least one selected from the group consisting of at least one inorganic acid selected from the group consisting of nitric acid, sulfuric acid, hydrochloric acid, acetic acid and phosphoric acid, ammonia, KOH, NH$_4$OH, amine, a transition metal alkoxide, and a tin compound, may be provided.

According to the twenty-first embodiment of the present invention, the epoxy composition of the nineteenth embodiment, in which the reaction catalyst is used by 0.01 to 0.1 equivalents based on 1 equivalent of an alkoxysilyl group of the epoxy compound having an alkoxysilyl group, may be provided.

According to the twenty-second embodiment of the present invention, the epoxy composition of the nineteenth embodiment, in which water is further included, may be provided.

According to the twenty-third embodiment of the present invention, there is provided an electronic material including the epoxy composition according to any one of the second to twenty-second embodiments.

According to the twenty-fourth embodiment of the present invention, there is provided a substrate including the epoxy composition according to any one of the second to twenty-second embodiments.

According to the twenty-fifth embodiment of the present invention, there is provided a film including the epoxy composition according to any one of the second to twenty-second embodiments.

According to the twenty-sixth embodiment of the present invention, there is provided a laminate including a metal layer placed on a base layer formed by using the epoxy composition according to any one of the second to twenty-second embodiments.

According to the twenty-seventh embodiment of the present invention, there is provided a printed circuit board including the laminate of the twenty-sixth embodiment.

According to the twenty-eighth embodiment of the present invention, there is provided a semiconductor device including the printed circuit board of the twenty-seventh embodiment.

According to the twenty-ninth embodiment of the present invention, there is provided a semiconductor packaging material including the epoxy composition according to any one of the second to twenty-second embodiments.

According to the thirtieth embodiment of the present invention, there is provided a semiconductor device including the semiconductor packaging material according to the twenty-ninth embodiment.

According to the thirty-first embodiment of the present invention, there is provided an adhesive including the epoxy composition according to any one of the second to twenty-second embodiments.

According to the thirty-second embodiment of the present invention, there is provided a paint composition including the epoxy composition according to any one of the second to twenty-second embodiments.

According to the thirty-third embodiment of the present invention, there is provided a composite material including the epoxy composition according to any one of the second to twenty-second embodiments.

According to the thirty-fourth embodiment of the present invention, there is provided a prepreg including the epoxy composition according to any one of the second to twenty-second embodiments.

According to the thirty-fifth embodiment of the present invention, there is provided a laminate including a metal layer placed on the prepreg of the thirty-fourth embodiment.

According to the thirty-sixth embodiment of the present invention, there is provided a cured product of the epoxy composition according to any one of the second to twenty-second embodiments.

According to the thirty-seventh embodiment of the present invention, the cured product of the thirty-sixth embodiment, in which the cured product has a coefficient of thermal expansion of 60 ppm/° C. or less, may be provided.

According to the thirty-eighth embodiment of the present invention, the cured product of the thirty-sixth embodiment, in which the cured product has a glass transition temperature of 100° C. or over, or does not exhibit the glass transition temperature, may be provided.

According to the thirty-ninth embodiment of the present invention, there is provided a method of preparing an epoxy compound having an alkoxysilyl group of the following Formula 1, including reacting an epoxy compound of the following Formula 4 and an alkene compound of the following Formula 6 in the presence of a solvent and a base to prepare an intermediate of the following Formula 5, and reacting the intermediate of the following Formula 5 and an alkoxysilane compound of the following Formula 7a in the presence of a platinum catalyst and an optional solvent.

[Formula 1]

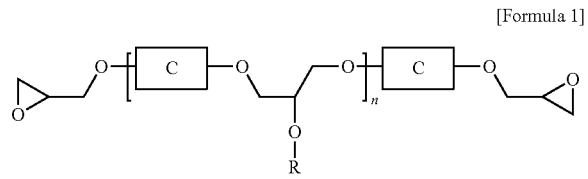

In Formula 1, a core unit C is independently selected from structures of the following Formulae 2-1 to 2-5, and each of the core unit C of a plurality of the core units C present in the above Formula 1 may be the same or different.

[Formula 2-1]

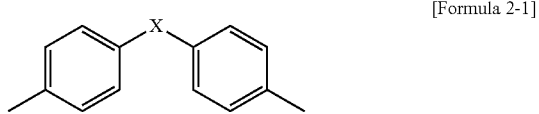

[Formula 2-2]

[Formula 2-3]

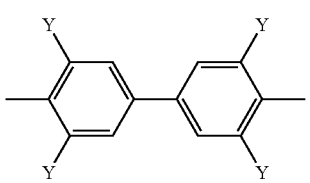

[Formula 2-4]

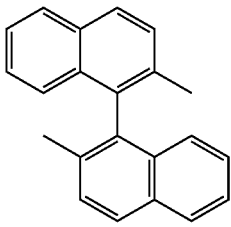

[Formula 2-5]

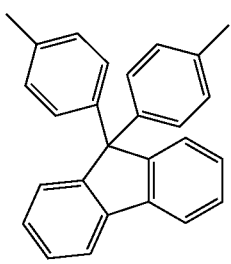

In Formula 2-1, X is —$CH_2$—, —$C(CH_3)_2$—, —$C(CF_3)_2$—, —S— or —$SO_2$—.

In Formula 2-3, Y is independently selected from the group consisting of H and an alkyl group of C1 to C5.

Here, n is an integer from 1 to 10, in the case that n is 1, R has a structure of the following Formula 3a, and in the case that n is at least 2, at least one R of a plurality of R has a structure of the following Formula 3a, and the remainder thereof are hydrogen atoms.

—$(CH_2)_m$—$SiR_aR_bR_c$      [Formula 3a]

In Formulae 3a, at least one of $R_a$ to $R_c$ is an alkoxy group having 1 to 5 carbon atoms, and the remainder thereof are alkyl groups having 1 to 10 carbon atoms, the alkoxy group and the alkyl group may be a linear chain or a branched chain alkoxy group or alkyl group, and m is an integer from 3 to 10.

[Formula 4]

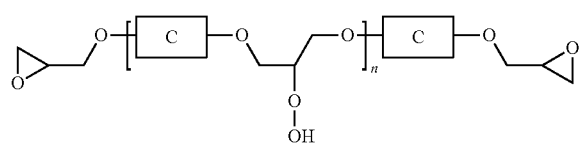

[Formula 5]

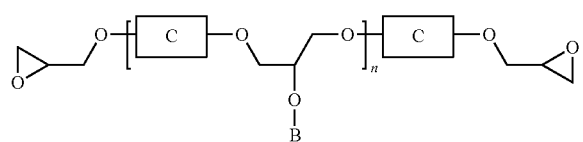

In the above Formulae 4 and 5, a core unit C and n are the same as defined in the above Formula 1, in the above Formula 5, in the case that n is 1, B is —$(CH_2)_l$—$CH$=$CH_2$ (l is an integer from 1 to 8), and in the case that n is at least 2, at least one of B is —$(CH_2)_l$—$CH$=$CH_2$ (l is an integer from 1 to 8), and the remainder thereof are hydrogen atoms.

X—$(CH_2)_l$—$CH$=$CH_2$      [Formula 6]

In Formula 6, l is an integer from 1 to 8, X is a halide such as Cl, Br or I, —O—$SO_2$—$CH_3$, —O—$SO_2$—$CF_3$, or —O—$SO_2$—$C_6H_4$—$CH_3$.

$HSiR_aR_bR_c$      [Formula 7a]

In Formula 7a, at least one of $R_a$ to $R_c$ is an alkoxy group having 1 to 5 carbon atoms, and the remainder thereof are alkyl groups having 1 to 10 carbon atoms, and the alkoxy group and the alkyl group may be a linear chain or a branched chain alkoxy group or alkyl group.

According to the fortieth embodiment of the present invention, the method of preparing an epoxy compound having an alkoxysilyl group of the thirty-ninth embodiment, in which 0.1 to 5 equivalents of an alkenyl group react with 1 equivalent of a hydroxyl group of the epoxy compound of the above Formula 4 during the first step, may be provided.

According to the forty-first embodiment of the present invention, the method of preparing an epoxy compound having an alkoxysilyl group of the thirty-ninth embodiment, in which the first step is performed at a temperature from 0° C. to 100° C. for 1 to 120 hours, may be provided.

According to the forty-second embodiment of the present invention, the method of preparing an epoxy compound having an alkoxysilyl group of the thirty-ninth embodiment, in which 1 to 5 equivalents of the alkoxysilane compound of the above Formula 7a react with 1 equivalent of an alkenyl group of the intermediate of the above Formula 5 during the second step, may be provided.

According to the forty-third embodiment of the present invention, the method of preparing an epoxy compound having an alkoxysilyl group of the thirty-ninth embodiment, in which the second step is performed at a temperature from room temperature to 120° C. for 1 to 72 hours, may be provided.

Advantageous Effects

Chemical bonding may be formed through the chemical reaction between an alkoxysilyl group and a filler (fiber and/or particles) and the chemical reaction between alkoxysilyl groups in the composite and/or the cured product of a novel epoxy composition including an epoxy compound having an alkoxysilyl group according to the present invention. Due to the chemical bonding, heat resistance properties may be improved. That is, the CTE of an epoxy composite may be decreased, and a glass transition temperature may be increased or the glass transition temperature may not be exhibited (hereinafter, 'Tg-less'). In addition, a cured product including the epoxy compound having an alkoxysilyl group in accordance with the present invention may show good flame retardant properties through the introduction of the alkoxysilyl group.

Further, when the epoxy composition is applied in a metal film of a substrate, good adhesive properties may be exhibited with respect to the metal film due to the chemical bonding between the functional group at the surface of the metal film and the alkoxysilyl group. In addition, due to the increase in chemical bonding efficiency of the composition including the alkoxysilylated epoxy compound, a silane coupling agent used in a common epoxy composition may be unnecessarily in the composition including the alkoxysilylated epoxy compound. The epoxy composition including the epoxy compound may have good curing efficiency, and a composite formed through the curing thereof may exhibit good thermal expansion properties such as a low CTE and a high glass transition temperature or Tg-less.

DESCRIPTION OF DRAWINGS

The above and other embodiments, features and other advantages of the present invention will be more clearly understood from the following detailed description taken in conjunction with the accompanying drawings, in which:

FIG. 1 is a graph illustrating dimensional change with respect to the change of the temperature of a composite according to Example 1;

FIG. 2 is a graph illustrating dimensional change with respect to the change of the temperature of a composite according to Comparative Example 1; and FIG. 3 is photographic images illustrating the evaluation results on flame retardant properties of composites according to Example 1 and Comparative Example 1.

BEST MODE FOR INVENTION

Exemplary embodiments of the present invention will now be described in detail with reference to the accompanying drawings.

The disclosure may, however, be exemplified in many different forms and should not be construed as being limited to the specific embodiments set forth herein. Rather, these embodiments are provided so that this disclosure will be thorough and complete, and will fully convey the scope of the disclosure to those skilled in the art.

The present invention provides a novel alkoxysilylated epoxy compound, a composite obtained by curing thereof exhibiting improved heat resistance properties, particularly a low CTE and a high Tg or Tg-less and/or a cured product thereof exhibiting good flame retardant properties, an epoxy composition including the same, a cured product formed by using the composition, a use of the composition, and a method of preparing the alkoxysilylated epoxy compound.

In the present invention, "composite" refers to a cured product formed by using a composition including an epoxy compound and a filler (fiber and/or inorganic particles). In the present invention, "cured product" refers to a cured product formed by using a composition including an epoxy compound as having general meaning, for example, a cured product formed by using a composition including an epoxy compound and a curing agent, and at least one selected from the group consisting of a filler, an additional curing agent, an optional curing accelerator and other additives. In addition, the term "cured product" is also used to denote a "half-cured product". Generally, only a cured product reinforced with inorganic particles or a fiber is referred to as a composite. Thus, the cured product has a broader meaning than the composite. The cured product reinforced with the inorganic particles or the fiber may be considered to have the same meaning as the composite.

When forming a composite through curing the alkoxysilylated epoxy compound in accordance with the present invention, an epoxy group may react with a curing agent to conduct a curing reaction, and the alkoxysilyl group may form bonding at an interface with the surface of the filler (fiber and/or inorganic particles) and/or a chemical bonding between alkoxysilyl groups. Thus, very high chemical bonding efficiency in an epoxy composite system may be obtained, and thus, a low CTE and high glass transition temperature increasing effect or Tg-less may be achieved. Therefore, dimensional stability may be improved. In addition, additional silane coupling agents are not necessary. Further, the cured product including the alkoxysilylated epoxy compound according to the present invention may exhibit good flame retardant property.

In addition, when applying the epoxy composition of the present invention on a chemically-treated metal film such as a copper film, a chemical bonding may be formed with a —OH group or the like at the surface of the metal produced through the metal surface treatment, thereby showing good adhesion with the metal film.

Hereinafter, an alkoxysilylated epoxy compound, an epoxy composition including the same, a cured product thereof, a use thereof, and a method of preparing the alkoxysilylated epoxy compound according to an embodiment of the present invention will be described in detail.

1. Alkoxysilylated Epoxy Compounds

In accordance with one embodiment of the present invention, a novel epoxy compound having a structure of the following Formula 1 is provided.

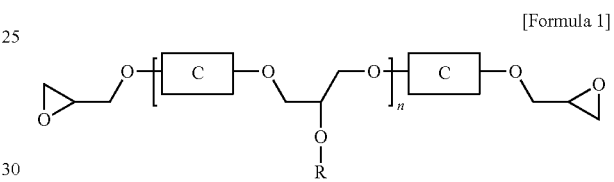

[Formula 1]

In Formula 1, a core unit C is independently selected from structures of the following Formulae 2-1 to 2-5, and each core unit C of a plurality of the core units C present in the above Formula 1 may be the same or different.

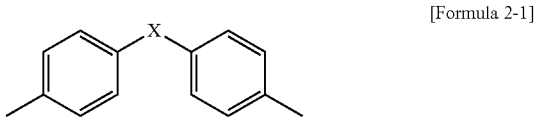

[Formula 2-1]

[Formula 2-2]

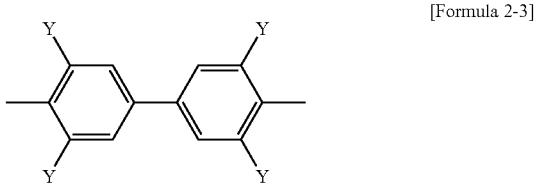

[Formula 2-3]

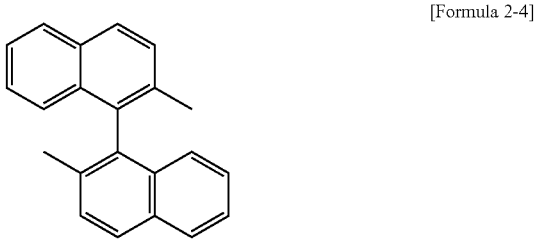

[Formula 2-4]

[Formula 2-5]

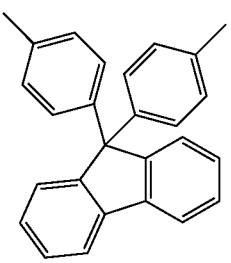

In Formula 2-1, X is —CH$_2$—, —C(CH$_3$)$_2$—, —C(CF$_3$)$_2$—, —S— or —SO$_2$—.

In Formula 2-3, Y is independently selected from the group consisting of H and an alkyl group of C1 to C5, n is an integer from 1 to 10, in the case that n is 1, R has a structure of the following Formula 3a or 3b, in the case that n is at least 2, at least one R of a plurality of R has a structure of the following Formula 3a or 3b, and the remainder thereof are hydrogen atoms, and an epoxy compound containing all core units having the above Formula 2-1 in which X is —C(CH$_3$)$_2$—, and R is the following Formula 3b is excluded from the epoxy compound of the above Formula 1.

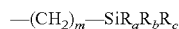 [Formula 3a]

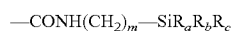 [Formula 3b]

In Formulae 3a and 3b, at least one of R$_a$ to R$_c$ is an alkoxy group having 1 to 5 carbon atoms, preferably an ethoxy group, and the remainder thereof are alkyl groups having 1 to 10 carbon atoms, the alkoxy group and the alkyl group may be a linear chain or a branched chain alkoxy group or alkyl group, and m is an integer from 3 to 10.

The term "alkoxy group" used in the present application refers to a monovalent —OR (R is an alkyl) group which may be a linear chain or a branched chain.

The term "alkyl group" used in the present application refers to a monovalent hydrocarbon group which may have a linear chain or a branched chain.

The core unit C of repeating units composing the epoxy compound of the above Formula 1 is selected from the structures of Formulae 2-1 to 2-5. Particularly, a plurality of core units C composing the epoxy compound of the above Formula 1 may be independently selected from the group consisting of the structures of Formulae 2-1 to 2-5. Thus, the plurality of core units C may have the same or different structures. The term "different structure" used in the present application includes a structure having the same core structures with different kinds of substituents and connection positions in Formula 1 as well as a different structure having different cores. For example, the structure may include the core of the above Formula 2-1 and the core of the above Formula 2-2 as the core units as the structure having the different cores. The structure having the different kind of substituents may include, for example, a core structure in which X is —CH$_2$— and a core structure in which X is —C(CH$_3$)$_2$ in the above Formula 2-1. The structure having the different connecting position of the core may include the core structure of Formula 2-2 connected to the core unit of the above Formula 1 through 1,6 positions and the core structure of Formula 2-2 connected to the core unit of the above Formula 1 through 2,7 positions.

The plurality of core units C may include core units having, for example, two different structures (will refer to C1 and C2 for convenience), without limitation. In this case, an epoxy compound including a repeating unit of a core unit C1 and a repeating unit of a core unit C2 may be an alternating copolymer having the following Formula 1A, a block copolymer having the following Formula 1B, or a random copolymer having the following Formula 1C.

[Formula 1A]

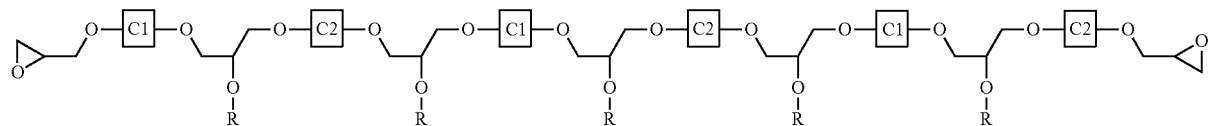

[Formula 1B]

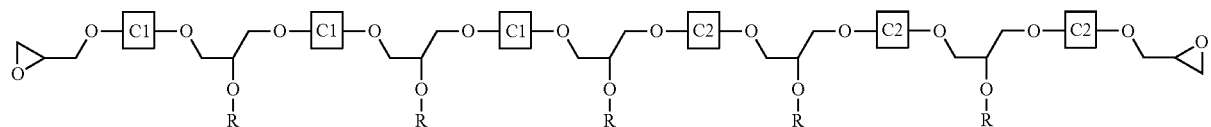

[Formula 1C]

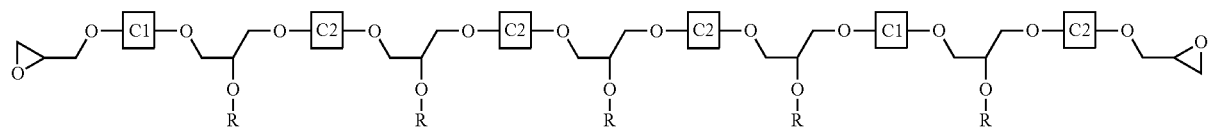

2. Epoxy Compositions

According to another embodiment of the present invention, there is provided a composition including a novel alkoxysilylated epoxy compound of the above Formula 1 according to the present invention. In a certain composition including a novel alkoxysilylated epoxy compound of the above Formula 1 according to an embodiment described later, an epoxy compound in which all of the core units are Formula 2-1 in which X is —C(CH$_3$)$_2$ and R is the following Formula 3b may not be excluded from the epoxy compound of the above Formula 1. In a composition including the novel alkoxysilylated epoxy compound of Formula 1 according to another embodiment described later, an epoxy compound in which all of the core units are Formula 2-1 in which X is —C(CH$_3$)$_2$ and R is the following Formula 3b may be excluded from the epoxy compound of the above Formula 1.

Any compositions provided in the present invention may be used in various uses such as an electronic material, for example, a semiconductor substrate such as an IC substrate, a build-up film, EMC (epoxy molding compound) which an encapsulating material (packaging material), an electronic part such as a printed circuit board, an adhesive, a paint composition, a composite material, or the like, without limitation. In addition, any compositions provided in the present invention may be a curable composition and/or a curable composition including an inorganic material.

Any epoxy compositions according to any embodiments described above or later in the present invention may include any kind and/or any mixing ratio known in the art only when including a novel epoxy compound of the above Formula 1 (hereinafter an 'epoxy compound of the present invention'). In this case, the kind and the mixing ratio of the curing agent, the curing accelerator (catalyst), the inorganic material (filler) (for example, inorganic particles and/or a fiber), other common epoxy compounds and other additives are not limited.

Further, the epoxy composition, the cured product and/or the composite may be used with various kinds of common epoxy compounds in consideration of the controlling feature of physical properties according to the application and/or use thereof. Thus, in the epoxy compositions according to any embodiments described above or later in the present invention, the epoxy compound may include an alkoxysilylated epoxy compound of the above Formula 1, and any kind of epoxy compound commonly known in this art (hereinafter a 'common epoxy compound').

The common epoxy compounds may be any epoxy compounds commonly known in this art without limitation, and may be, for example, at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound. Further, the common epoxy compound may be at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound including bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, an aminophenol cyclo aliphatic compound, or a novolak unit, as a core structure.

For example, the common epoxy compound may be at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound including bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, an aminophenol cyclo aliphatic compound, or a novolak unit, as a core structure.

Any epoxy compositions in accordance with an embodiment of the present invention may include without limitation, based on the total amount of an epoxy compound, from 1 wt % to 100 wt % of the epoxy compound according to any embodiments of the present invention and from 0 wt % to 99 wt % of the common epoxy compound; for example, from 10 wt % to 100 wt % of the epoxy compound of the present invention and from 0 wt % to 90 wt % of the common epoxy compound; for example, from 30 wt % to 100 wt % of the epoxy compound of the present invention and from 0 wt % to 70 wt % of the common epoxy compound; for example, from 50 wt % to 100 wt % of the epoxy compound of the present invention and from 0 wt % to 50 wt % of the common epoxy compound; for example, from 10 wt % to below 100 wt % of the epoxy compound of the present invention and from excess of 0 wt % to 90 wt % of the common epoxy compound; for example, from 30 wt % to below 100 wt % of the epoxy compound of the present invention and from excess of 0 wt % to 70 wt % of the common epoxy compound; for example, from 50 wt % to below 100 wt % of the epoxy compound of the present invention and from excess of 0 wt % to 50 wt % of the common epoxy compound.

Further, in accordance with an embodiment of the present invention, an epoxy composition including an epoxy compound of the above Formula 1 and an inorganic material (filler) (for example, inorganic particles and/or a fiber) according to any embodiments of the present invention (hereinafter a 'composite composition') is provided. The composite composition is considered to include an epoxy composition having any kind and/or any mixing ratio commonly known in this art only when including an alkoxysilylated epoxy compound of the above Formula 1 and the filler. The kinds and the mixing ratios of the curing agent, the curing accelerator (catalyst), the inorganic material (filler) (for example, inorganic particles and/or a fiber) composing the epoxy composition, and the kinds of the common epoxy compound and other additives are not limited.

The above-described composite composition and any compositions described above or later according to the present invention may additionally include inorganic particles.

Any inorganic particles known to be used to reinforce the physical properties of a common organic resin may be used. Examples of the inorganic particles may include, without limitation, at least one selected from the group consisting of at least one metal oxide selected from the group consisting of silica (including, for example, fused silica and crystalline silica), zirconia, titania, alumina, silicon nitride and aluminum nitride, T-10 type silsesquioxane, ladder type silsesquioxane, and cage type silsesquioxane. The inorganic particles may be used alone or as a mixture of two or more thereof.

In the case that particularly a large amount of the silica is mixed, the fused silica is preferably used. The fused silica may have any shape among a cataclastic shape and a spherical shape. However, the spherical shape is preferable to increase the mixing ratio of the fused silica and to restrain the increase of the fused viscosity of a forming material.

The inorganic particles having a particle size of 0.5 nm to several tens of μm (for example, from 50 μm to 100 μm) may be used in consideration of the use of a composite, particularly, the dispersibility of the inorganic particles, or the like. Since the inorganic particles are dispersed in the epoxy compound, and the dispersibility is different according to the particle size, the inorganic particles having the above-described size may preferably be used. In addition, the distribution range of the inorganic particles to be mixed is preferably increased to increase the mixing ratio of the inorganic particles.

In the epoxy composition in accordance with an embodiment of the present invention, the mixing amount of the inorganic particles with respect to the epoxy compound may be appropriately controlled in consideration of the CTE decrease of an epoxy composite and an appropriate viscosity required while applying. For example, the amount of the inorganic particles may be 5 wt % to 95 wt %, for example, 5 wt % to 90 wt %, for example, 10 wt % to 90 wt %, for example, 30 wt % to 95 wt %, for example, 30 wt % to 90 wt %, for example, 5 wt % to 60 wt %, for example, 10 wt % to 50 wt % based on the total amount of the solid content of the epoxy compound (based on the total amount of the epoxy cured product for the epoxy cured product).

More particularly, in an exemplary embodiment, when the epoxy composition is used as a semiconductor encapsulating agent, or the like, the amount of the inorganic particles may be, for example, 30 wt % to 95 wt %, for example, 30 wt % to 90 wt %, without limitation, based on the amount of the solid content of the epoxy compound (based on the total amount of the epoxy cured product for the epoxy cured product) in consideration of the CTE value and material processability. In other exemplary embodiments, when the epoxy composition is used in a semiconductor substrate, the amount of the inorganic particles may be 5 wt % to 60 wt %, for example, 10 wt % to 50 wt % based on the total solid content of the epoxy compound (based on the total amount of the epoxy cured product for the epoxy cured product) considering the CTE value and the modulus of the substrate.

Meanwhile, when the fiber is used as the inorganic material, a composite may be obtained by mainly an immersing method of the fiber with the epoxy composition. Thus, the size of the fiber may not be specifically limited. Any kind of fiber commonly used in this field may be used and dimensions thereof are not limited.

Any commonly used fibers used for improving physical properties of a common organic resin cured product may be used without limitation. Particularly, a glass fiber, an organic fiber or a mixture thereof may be used. In addition, the term 'glass fiber' used in this application may include a glass fiber fabric, a glass fiber non woven product, or the like, as well as the glass fiber. Examples of the glass fibers may include, without limitation, the glass fiber of an E-glass fiber, a T-glass fiber, an S-glass fiber, an NE-glass fiber, an E-glass fiber, a D-glass fiber, a quartz glass fiber, or the like. For example, the glass fiber of E or T may be included. An organic fiber may include at least one selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber. These fibers may be used alone or as a combination of two or more thereof.

The fiber content in the epoxy composition according to the present invention, for example, in a glass fiber composite epoxy composition, may be 10 wt % to 90 wt %, for example, 30 wt % to 70 wt %, in addition, for example, 35 wt % to 65 wt % based on the total weight of the solid content of the epoxy composition. In addition, the fiber content in the cured product of the epoxy composition, for example, in a glass fiber composite, may be 10 wt % to 90 wt %, for example, 30 wt % to 70 wt %, in addition, for example, 35 wt % to 65 wt % based on the total amount of the cured product. Thus, the resin content may be 10 wt % to 90 wt %, for example, 30 wt % to 70 wt %, in addition, for example, 35 wt % to 65 wt %. The fiber content within the above-described range may be preferred in consideration of the increase in heat resistance and the processability aspect. Meanwhile, in the epoxy composition, the cured product, or the like, including the fiber, solid parts excluding the fiber from the total solid content is referred to as the resin. In the epoxy composition including the fiber, the remaining amount other than the fiber is the resin content.

Further, in the epoxy composition including the fiber may additionally include inorganic particles as occasion demands. In this case, the inorganic particles may be included in an amount of 1 wt % to 70 wt % in the resin component based on the total resin content in consideration of the improvement of the physical properties and processability. In this case, the kind of the inorganic particles is not specifically limited, and any inorganic particles known in this art may be used. For example, the above-described inorganic particles may be used.

According to further another embodiment of the present invention, an epoxy composition including an alkoxysilylated epoxy compound of the above Formula 1 according to any embodiments of the present invention and a curing agent is provided (hereinafter a 'curing agent-containing composition'). Any curing agent-containing compositions may include an epoxy composition having any kind and/or any mixing ratio known in the art only when including an alkoxysilylated epoxy compound of the above Formula 1 and a curing agent. However, the kinds and the mixing ratios of the curing agent, the curing accelerator (catalyst), the inorganic material (filler) (for example, inorganic particles and/or fiber), other common epoxy compounds and other additives composing the epoxy composition are not limited.

According to further another embodiment of the present invention, an epoxy composition including an epoxy compound of the above Formula 1 according to any embodiments of the present invention and an alkoxysilyl reaction catalyst (hereinafter a 'reaction catalyst') is provided (hereinafter a 'reaction catalyst-containing composition'). Any reaction catalyst-containing compositions may include an epoxy composition having any kind and/or any mixing ratio known in the art only when including an alkoxysilylated epoxy compound of the above Formula 1 and a reaction catalyst. However, the kinds and the mixing ratios of the curing agent, the curing accelerator (catalyst), the inorganic material (filler) (for example, inorganic particles and/or fiber), other common epoxy compounds and other additives composing the epoxy composition are not limited. In the case that the alkoxysilyl reaction catalyst is included, improved processability (for example, a rapid curing rate and/or a low curing temperature) may be expected.

The curing agent-containing composition and the reaction catalyst-containing composition may also include the common epoxy compound as the epoxy compound. In this case, the kind of the common epoxy compound and the mixing ratios of the alkoxysilylated epoxy compound and the common epoxy compound are the same as described above.

When a curing agent is included in the curing agent-containing composition and the composition according to an embodiment of the present invention, any curing agents commonly known as a curing agent of an epoxy compound may be used. For example, an amine compound, a phenol compound, an anhydrous oxide compound may be used, without limitation.

More particularly, an aliphatic amine, an alicyclic amine, an aromatic amine, other amines and a modified amine may be used as the amine-based curing agent without limitation. In addition, an amine compound including two or more primary amine groups may be used. Particular examples of the amine curing agents may include at least one aromatic amine selected from the group consisting of 4,4'-dimethylaniline (diamino diphenyl methane, DAM or DDM), and diamino diphenyl sulfone (DDS), and m-phenylene diamine, at least one aliphatic amine selected from the group consisting of diethylene triamine (DETA), diethylene tetramine, triethylene tetramine (TETA), m-xylene diamine (MXTA), methane diamine (MDA), N,N'-diethylenediamine (N,N'-DEDA), tetraethylenepentaamine (TEPA), and hexamethylenediamine, at least one alicyclic amine selected from the group consisting of isophorone diamine (IPDI), N-aminoethyl piperazine (AEP), bis(4-amino 3-methylcyclohexyl) methane, and larominc 260, other amines such as dicyanamide (DICY), or the like, and a modified amine such as a polyamide-based compound, an epoxide-based compound, or the like.

Examples of the phenol curing agent may include, without limitation, a phenol novolak resin, a trifunctional phenol novolak resin, a cresol novolak resin, a bisphenol A novolak resin, a xylene novolak resin, a triphenyl novolak resin, a biphenyl novolak resin, a phenol p-xylene resin, a phenol 4,4'-dimethylbiphenylene resin, a phenol dicyclopentadiene novolak resin, a dicyclopentadiene-phenol novolak (DCPD-phenol) resin, a xylok (p-xylene modified) resin, a biphenyl-based phenol resin, a naphthalene-based phenol novolak resin, a triazine-based compound, dihydroxy naphthalene, dihydroxy benzene, or the like.

Examples of the anhydrous oxide-based curing agent may include, without limitation, an aliphatic anhydrous oxide such as dodecenyl succinic anhydride (DDSA), poly azelaic poly anhydride, or the like, an alicyclic anhydrous oxide such as hexahydrophthalic anhydride (HHPA), methyl tetrahydrophthalic anhydride (MeTHPA), methylnadic anhydride (MNA), or the like, an aromatic anhydrous oxide such as trimellitic anhydride (TMA), pyromellitic acid dianhydride (PMDA), benzophenonetetracarboxylic dianhydride (BTDA), or the like, and a halogen-based anhydrous compound such as tetrabromophthalic anhydride (TBPA), chlorendic anhydride, or the like.

In general, the crosslinking density of an epoxy composite may be controlled by the extent of reaction of the curing agent with the epoxy group. According to the target crosslinking density, the stoichiometric ratio of the curing agent to epoxy compound may be controlled. For example, when an amine curing agent is used, the stoichimetric equivalent ratio of the epoxy to amine may be preferably controlled to 0.5 to 2.0, for example, 0.8 to 1.5 in an reaction of the amine curing agent with the epoxy group.

Though the mixing ratio of the curing agent has been explained with respect to the amine curing agent, a phenol curing agent, an anhydrous oxide curing agent and any curing agents for curing epoxy compounds not separately illustrated in this application but used for curing may be used by appropriately mixing a stoichiometric amount according to the chemical reaction of the epoxy functional group and the reactive functional group of the curing agent based on the concentration of the total epoxy group in the epoxy composition according to the desired range of the crosslinking density. The above-described parts are commonly known in this field.

As a cationic photocuring agent (also referred to as a photo initiator), any photocuring agents commonly known in this field may be used, without limitation, for example, an aromatic phosphate, an aromatic iodide, an aromatic sulfonate, etc. Particularly, diphenyl iodonium tetrakis(pentafluorophenyl)borate, diphenyl iodonium hexafluorophosphate, diphenyl iodonium hexafluoroantimonate, di(4-nonylphenyl)iodonium hexafluorophosphate, triphenylsulfonium hexafluorophosphate, triphenylsulfonium hexafluoroantimonate, triphenylsulfonium tetrakis(pentafluorophenyl)borate, 4,4'-bis[diphenylsulfonio]diphenylsulfide bishexafluorophosphate, 4,4'-bis[di($\beta$-hydroxyethoxy)phenylsulfonio]diphenylsulfide bishexafluoroantimonate, 4,4'-bis[di($\beta$-hydroxyethoxy)phenylsulfonio]diphenylsulfide bishexafluorophosphate, etc., may be used. In general, the photocurable agent may be used in a ratio of 0.5 to 20 phr (parts per hundred parts of resin, parts per weight with respect to 100 parts by weight of the epoxy compound), preferably at least 1 phr, and preferably at most 15 phr with respect to the epoxy compound.

An optional curing accelerator (catalyst) may be additionally included as occasion demands to promote the curing reaction in any epoxy compositions provided in the present invention. Any curing accelerators (catalysts) commonly used for curing an epoxy composition in this art may be used without limitation, for example, an imidazole-based, a tertiary amines, a quaternary ammonium compounds, an organic acid salt, a phosphorous compounds may be used as curing accelerators.

More particularly, for example, the imidazole-based curing accelerator such as dimethylbenzylamine, 2-methylimidazole (2MZ), 2-undecylimidazole, 2-ethyl-4-methylimidazole (2E4M), 2-phenylimidazole, 1-(2-cyanoethyl)-2-alkyl imidazole, and 2-heptadecylimidazole (2HDI); the tertiary amine-based curing accelerator such as benzyldimethylamine (BDMA), tris dimethylaminomethyl phenol (DMP-30), and triethylenediamine; the quaternary ammonium-based curing accelerator such as tetrabutylammonium bromide, or the like; diazabicycloundecene (DBU), or an organic acid of DBU; the phosphor compound-based curing accelerator such as triphenyl phosphine, phosphoric acid ester, or the like, and a Lewis acid such as $BF_3$-monoethylamine ($BF_3$-MEA), or the like, may be illustrated without limitation. Latent curing accelerators may also be used, which are provided by microcapsulating the accelerators and forming complex salts with accelerators, for example. These compounds may be used alone or as a mixture of two or more thereof according to curing conditions.

The mixing amount of the curing accelerator may be a commonly applied mixing amount in this art without limitation. For example, 0.1 to 10 phr, for example, 0.2 to 5 phr of the curing accelerator based on the epoxy compound may be used. The above-described range of the curing accelerator may be preferably used in consideration of curing reaction accelerating effect and the control of curing reaction rate. Through using the above-described range of the curing accelerator, the curing may be rapidly achieved, and the improvement of working throughput may be expected.

When the reaction catalyst for alkoxysilyl group is included in the reaction catalyst-containing composition and a composition according to any embodiments of the present invention, the reaction catalyst for alkoxysilyl group may be at least one selected from the group consisting of at least one inorganic acid selected from the group consisting of, for example, nitric acid, sulfuric acid, hydrochloric acid, acetic acid and phosphoric acid, ammonia, KOH, $NH_4OH$, amine, a transition metal alkoxide, and a tin compound (for example, dibutyltin dilaurate and/or tin(II) 2-ethylhexanoate, or the like), without limitation. The mixing ratio of the reaction catalyst for alkoxysilyl group is not specifically limited; however, 0.01 to 0.1 equivalents of the alkoxysilyl reaction catalyst may be included with respect to 1 equivalent of the alkoxysilyl group.

In the composition including the reaction catalyst for alkoxysilyl group, water may be additionally included to increase the efficiency of the alkoxysilyl reaction catalyst. The mixing ratio of is not specifically limited; however, 0.01 to 20 equivalents of water may be included with respect to 1 equivalent of the alkoxysilyl group.

In the epoxy composition, other additives such as a releasing agent, a surface treating agent, a flame retardant, a plasticizer, bactericides, a leveling agent, a defoaming agent, a colorant, a stabilizer, a coupling agent, a viscosity controlling agent, a diluent, or the like may be mixed to control the physical properties of the epoxy composition within the range of undamaging the physical properties of the epoxy composition as occasion demands.

As described above, the term "epoxy composition" used in the present application is understood to include an epoxy compound of the present invention and other constituents composing the epoxy composition, for example, an optional curing agent, a curing accelerator (catalyst), an inorganic material (filler) (for example, inorganic particles and/or a fiber), other common epoxy compounds, a solvent and other additives mixed as occasion demands in this field. In general, the solvent may be optionally used to control the amount and/or the viscosity of the solid content of the epoxy composition in consideration of the processability of the epoxy composition, and the like. Meanwhile, the term "total amount of the solid content of the epoxy composition" in the present invention is used to denote the total amount of solid components other than liquid components such as solvents from the components composing the epoxy composition.

The epoxy composition provided in accordance with an exemplary embodiment of the present invention may be used as an electronic material. The electronic material may include, for example, a substrate for a semiconductor, a film, a prepreg, a laminate obtained by placing a metal layer on a base layer formed by using the composition of the present invention, a substrate, an encapsulating material (a packaging material), a build-up film (substrate), a printed circuit board, or the like. In addition, the epoxy composition may be used in various applications such as an adhesive, a paint composition and a composite material. In accordance with other exemplary embodiments of the present invention, an electronic material including or manufactured using a composition including the alkoxysilylated epoxy compound of the present invention is provided. Further, a semiconductor apparatus including or manufactured using the electronic material, is provided. Particularly, the semiconductor apparatus may be a semiconductor apparatus including a printed circuit board (for example, for installing a semiconductor device) including or manufactured using the composition including the alkoxysilylated epoxy compound of the present invention and/or may be a semiconductor apparatus including a semiconductor packaging material. In addition, a curing agent, an adhesive, a paint composition or a composite material including or manufactured using any epoxy compositions provided in any embodiments of the present invention, may be provided.

In accordance with other exemplary embodiments of the present invention, a cured product including or manufactured using the epoxy composition provided in accordance with an exemplary embodiment of the present invention may be provided. In the case that applying the epoxy composition provided in an exemplary embodiment of the present invention is practically used, for example, when the epoxy composition is applied as the electronic material, or the like, a cured product formed of the epoxy composition may be used. In this art, the cured product formed of the composition including the epoxy compound and the filler of the inorganic component may be commonly referred to as a composite.

The alkoxysilylated epoxy compound provided in above-described exemplary embodiments of the present invention may show good heat resistance in the composite and/or good flame retardant property in the cured product.

Particularly, the composite may exhibit a low CTE, for example, 15 ppm/° C. or less, for example, 12 ppm/° C. or less, for example, 10 ppm/° C. or less, for example, 8 ppm/° C. or less, for example, 6 ppm/° C. or less, for example, 4 ppm/° C. or less. The physical properties of the composite are good when the CTE value is small, and the lower value of the CTE is not particularly limited.

For example, a composite including any alkoxysilylated epoxy compounds in accordance with exemplary embodiments of the present invention as the epoxy compound, and a glass fiber, for example, an E-glass fiber and/or a T-glass fiber as the inorganic material, and having the resin content (the resin content may or may not include inorganic particles) of 30 wt % to 60 wt % may have a CTE of 10 ppm/° C. or less, for example, 8 ppm/° C. or less, for example, 6 ppm/° C. or less, for example, 4 ppm/° C. or less.

In addition, for example, a composite including an alkoxysilylated epoxy compound in accordance with exemplary embodiments of the present invention as the epoxy compound, and inorganic particles as the inorganic material, for example, silica particles of 60 wt % to 80 wt %, for example, 70 wt % to 80 wt %, may have a CTE of 20 ppm/° C. or less, for example, 15 ppm/° C. or less, for example, 10 ppm/° C. or less, for example, 8 ppm/° C. or less, for example, 6 ppm/° C. or less, for example, 4 ppm/° C. or less.

In addition, Tg of the composite (a cured product including an inorganic material) according to the present invention may be higher than 100° C., for example, 130° C. or over, in addition, for example, 250° C. or over. Otherwise, the composite may be Tg-less. The physical properties of the composite are good when the Tg value is large, and the upper value of the Tg is not particularly limited.

Meanwhile, the cured product formed by using the alkoxysilylated isocyanurate epoxy compound itself (a cured product excluding an inorganic material) according to the present invention may have a CTE of 50 ppm/° C. to 150 ppm/° C.

In the present application, the values limited by the range include the lower limit, the upper limit, any sub ranges in the range, and all numerals included in the range, unless otherwise specifically stated. For example, C1 to C10 is understood to include all of C1, C2, C3, C4, C5, C6, C7, C8, C9 and C10. In addition, in the case when the lower limit or the upper limit of the numerical range is not defined, it would be found that the smaller or the larger value may provide the better properties. In addition, in the case when the limit is not defined, any values may be included. For example, CTE of 4 ppm/° C. or less is understood to include every value in the range such as the CTE of 4, 3.5, 3, 2.7, 2, 1.4, 1, 0.5 ppm/° C., or the like.

3. Method of Preparing Alkoxysilylated Epoxy Compounds

The alkoxysilylated epoxy compounds of the above Formula 1 according to an embodiment of the present invention may be prepared by the following methods.

(1) Method of Preparing an Epoxy Compound of Formula 1 in which R is Formula 3a (Preparation Method 1)

According to another embodiment of the present invention, a method of preparing an epoxy compound of Formula 1 in which R is Formula 3a is provided. First, in the first step, an intermediate of the following Formula 5 alkenylated with the epoxy compound of Formula 4 is obtained by reacting an epoxy compound of the following Formula 4 which is the basic structure of the epoxy compound having an alkoxysilyl group of the above Formula 1 with an alkene compound of the following Formula 6. By the alkenylation in the first step, the hydroxyl group of the epoxy compound of Formula 4 is dehydrogenated and alkenylated to form the intermediate of the following Formula 5.

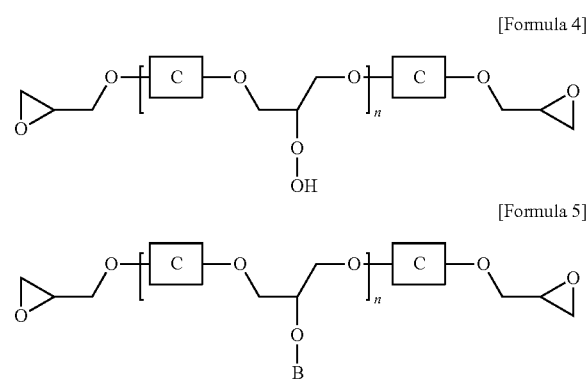

[Formula 4]

[Formula 5]

In the above Formulae 4 and 5, C and n are the same as defined in the above Formula 1. In Formula 5, in the case that n is 1, B is —$(CH_2)_l$—CH=$CH_2$ (l is an integer from 1 to 8), and preferably, an integer from 1 to 4, and in the case that n is at least 2, at least one of B is —$(CH_2)_l$—CH=$CH_2$ (l is an integer from 1 to 8), and preferably, an integer from 1 to 4, and the remainder thereof are hydrogen atoms. Each core unit C of the plurality of core units C in the compound of the above Formulae 4 and 5 may be the same or different as in the epoxy compound of the above Formula 1.

X—$(CH_2)_l$—CH=$CH_2$     [Formula 6]

In Formula 6, l is an integer from 1 to 8, and preferably, an integer from 1 to 4, X is a halide such as Cl, Br or I, —O—$SO_2$—$CH_3$, —O—$SO_2$—$CF_3$, or —O—$SO_2$—$C_6H_4$—$CH_3$.

The alkenylation reaction in the first step is performed by reacting the epoxy compound of the above Formula 4 and the alkene compound of the above Formula 6 in the presence of a solvent and a base. The reaction in the first step may be performed by reacting the epoxy compound of the above Formula 4 and the alkene compound of the above Formula 6 at 0 to 100° C. for 1 to 120 hours.

In the reaction of the first step, the epoxy compound of Formula 4 and the alkene compound react so that a hydroxyl group and an alkenyl group react by the stoichiometric equivalent ratios. Thus, the reaction is performed so that 0.1 to 5 equivalents of the alkenyl group of the alkene compound react with 1 equivalent of the hydroxyl group of the epoxy compound of the above Formula 4. However, the number of the hydroxyl groups in the epoxy compound may be changed according to the number of the repeating units of the epoxy compound of the above Formula 4. In the case that at least two hydroxyl groups are present, at least one hydroxyl group of the plurality of hydroxyl groups may react with the alkene compound. In this case, less than 1 equivalent of the alkene compound, that is, about 0.1 equivalents thereof may be used. A person skilled in the art may appropriately control the equivalents of the alkene compound in consideration of the desired alkenylation degree of the intermediate of Formula 5 from the above-described factors.

It is described above that the alkenylation in the first step is performed by reacting the epoxy compound of Formula 4 with the alkene compound in the presence of a solvent and a base. Particularly, the epoxy compound of Formula 4, the alkene compound and the base may be added subsequently, all the reacting materials may be added once, or the alkene compound may be added after dehydrogenating the epoxy compound of Formula 4 with a time interval to perform reaction. The dehydrogenation is a commonly known process in the synthesis of chemical materials, and so, a person skilled in the art may perform the reaction by appropriately adding the reacting materials so that the intermediate of Formula 5 may be formed by the dehydrogenation of the hydroxyl group of Formula 4 and the reaction of the dehydrogenated epoxy compound of Formula 4 with the alkene compound.

The reaction temperature and the reaction time of the alkenylation are dependent on the structure of the epoxy compound of Formula 4, and may be changed according to the epoxy compound of Formula 4. For example, the intermediate of Formula 5 may be obtained by the reaction at 0 to 100° C. for 1 to 120 hours.

The solvents used during the reaction of the first step may be any organic solvents only if able to dissolve the reacting materials well, not inducing any adverse influence to the reaction, and being easily removed after the reaction. For example, acetonitrile, tetrahydrofuran (THF), methyl ethyl ketone (MEK), dimethylformamide (DMF), dimethyl sulfoxide (DMSO), methylene chloride (MC), toluene, or the like, may be used. These solvents may be used alone or as a mixture of two or more thereof. The amount and/or the concentration of the solvent may not be limited to a specific range, and an appropriate amount and/or concentration of the solvent may be used within a range for sufficiently dissolving the reacting materials and not adversely affecting the reaction. A person skilled in the art may select an appropriate amount of the solvent in consideration of the above-mentioned points.

The base used in the reaction of the first step may include, for example, NaH, KOH, NaOH, $K_2CO_3$, $KHCO_3$, $Na_2CO_3$, $NaHCO_3$, triethylamine, and diisopropylethylamine, without limitation. These bases may be used alone or as a combination of two or more thereof. 0.1 to 5 equivalents of the base may be used based on 1 equivalent of the hydroxyl functional group of epoxy compound of Formula 4 in consideration of reaction efficiency.

Then, in the reaction of the second step, the epoxy compound having an alkoxysilyl group of Formula 1 in which R is Formula 3a is obtained by performing a reaction of the intermediate of the above Formula 5 obtained in the reaction of the first step with an alkoxysilane compound of the following Formula 7a. In this case, as described above, in the case that n is 1 in Formula 1, R is the above Formula 3a, and in the case that n is at least 2, at least one of a plurality of R is 3a, and the remainder thereof may be hydrogen atoms.

$HSiR_aR_bR_c$     [Formula 7a]

In the above Formula 7a, at least one of $R_a$ to $R_c$ is an alkoxy group having 1 to 5 carbon atoms, and preferably is an ethoxy group, and the remainder thereof are an alkyl group having 1 to 10 carbon atoms. The alkoxy group and the alkyl group may be a linear chain or a branched chain alkoxy group or alkyl group.

In the hydrosilylation in the reaction of the second step, the alkenyl of the above Formula 5 and the alkoxysilane compound react in the presence of a platinum catalyst and an optional solvent.

In the reaction of the second step, the intermediate of Formula 5 and the silane compound react so that the alkenyl group and hydrogen in the alkoxysilyl compound of Formula 7a react stoichiometrically, and 1 to 5 equivalents of the silane compound may react with respect to 1 equivalent of the alkenyl group of the above Formula 5 in consideration of the above-described points.

The reaction temperature and the reaction time of the second step are dependent on the kind of reacting materials. Particularly, the reaction of the second step is performed at a temperature from room temperature (for example, 15° C. to 25° C.) to 120° C. for 1 to 72 hours to obtain the epoxy compound having an alkoxysilyl group of Formula 1 in which R is Formula 3a.

The solvents may be optionally used as occasion demands in the reaction of the second step. For example, when the viscosity of the reacting materials at the reaction temperature is appropriate for conducting the reaction without a solvent in the second step reaction, the solvent may not be necessary. That is, when the viscosity of the reacting materials is sufficiently low that the mixing and the stirring of the reacting materials may be conducted smoothly without the solvent, the use of a solvent may not be necessary.

When the solvent is used, any aprotic solvents that may easily dissolve the reacting materials, that do not have any adverse effects, and that may be easily removed after the reaction, may be used without limitation. For example, toluene, acetonitrile, THF, MEK, DMF, DMSO, methylene chloride, or the like may be used, without limitation. These solvents may be used alone or as a mixture of two or more thereof. The amount and/or the concentration of the solvent may not be limited to a specific range, and an appropriate amount and/or concentration of the solvent may be used within a range for sufficiently dissolving the reactants and not adversely affecting the reaction. A person skilled in the art may select an appropriate amount of the solvent in consideration of the above-mentioned points.

In the reaction of the second step, the platinum catalyst may include, for example, $PtO_2$ or chloroplatinic acid ($H_2PtCl_6$), without limitation. $1 \times 10^{-4}$ to 0.05 equivalents of the platinum catalyst with respect to 1 equivalent of the alkenyl group of the intermediate of Formula 5 may be preferably used in consideration of reaction efficiency.

(2) Method of Preparing Epoxy Compound of Formula 1 in which R is Formula 3b (Preparation Method 2)

For reference, the epoxy compound of Formula 1 in which R is Formula 3b may be prepared by the following method. The epoxy compound of Formula 1 in which R is Formula 3b is prepared by the reaction of the epoxy compound of the above Formula 4 which is the basic structure of the epoxy compound having an alkoxysilyl group with an isocyanate-based alkoxysilane. The epoxy compound of the above Formula 4 and the isocyanate-based alkoxysilane of the following Formula 7b react in the presence of an optional solvent.

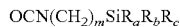   [Formula 7b]

In Formula 7b, m is an integer from 3 to 10, and preferably an integer from 3 to 6, at least one of $R_a$ to $R_c$ is an alkoxy group of C1-C5, and preferably an ethoxy group, and the remainder thereof are alkyl groups of C1-C10. The alkoxy group and the alkyl group may be a linear chain or a branched chain alkoxy group or alkyl group.

In the reaction of the epoxy compound of Formula 4 and the isocyanate-based alkoxysilane of Formula 7b, the hydroxyl group of the epoxy compound of Formula 4 and the alkoxysilane react stoichiometrically, and the epoxy compound of the above Formula 4 and the isocyanate-based alkoxysilane react so that 1 to 5 equivalents of the alkoxysilane may react with respect to 1 equivalent of the hydroxyl group of the epoxy compound of the above Formula 4 in consideration of the above-described points.

The reaction temperature and the reaction time of the reaction are dependent on the kind of reacting materials. For example, the reaction of the second step is performed at a temperature from room temperature (for example, 15° C. to 25° C.) to 120° C. for 1 to 72 hours to obtain the epoxy compound having an alkoxysilyl group of Formula 1 in which R is Formula 3b. As described above, in Formula 1, in the case that n is 1, R is the above Formula 3b, and in the case that n is at least 2, at least one of a plurality of R may be the above Formula 3b, and the remainder thereof may be hydrogen.

The reaction may be performed in the presence of a base as occasion demands. The reaction may be performed without using a base, however, the reaction rate may be slow. The reaction rate may be increased by using a base. The base used may include, for example, $K_2CO_3$, $Na_2CO_3$, $KHCO_3$, $NaHCO_3$, triethylamine, and diisopropylethylamine, without limitation. These bases may be used alone or as a combination thereof. 1 to 5 equivalents of the base may be used based on 1 equivalent of the hydroxyl group of the epoxy compound of Formula 1 when considering reaction efficiency.

The solvents may be optionally used as occasion demands. For example, when the viscosity of the reacting materials at the reaction temperature is appropriate for conducting the reaction without a solvent, the solvent may not be necessary. That is, when the viscosity of the reacting materials is sufficiently low that the mixing and the stirring of the reacting materials may be conducted smoothly without the solvent, the use of a solvent may not be necessary. This state may be easily understood by a person skilled in the art. When the solvent is used, any aprotic solvents that may easily dissolve the reacting materials, that do not have any adverse effects, and that may be easily removed after the reaction, may be used without limitation. For example, toluene, acetonitrile, THF, MEK, DMF, DMSO, methylene chloride (MC), or the like, may be used. These solvents may be used alone or as a mixture of two or more thereof. The amount and/or the concentration of the solvent may not be limited to a specific range, and an appropriate amount and/or concentration of the solvent may be used within a range for sufficiently dissolving the reacting materials and not adversely affecting the reaction. A person skilled in the art may select an appropriate amount of a solvent considering the above-mentioned points.

Hereinafter, the present invention will be described in more detail with reference to exemplary embodiments. The following exemplary embodiments are only illustrated for assisting in gaining an understanding of the present invention, and the present invention is not limited thereto.

Synthetic Example 1

Step (1)—Allylation of Hydroxyl Group 3 g of sodium hydride (60 wt %, dispersed in mineral oil) and 200 ml of DMF were added to a 1 L flask, followed by stirring and mixing at room temperature. Then, 38.0 g of an epoxy compound (diglycidyl ether of bisphenol A (DGEBA) (EEW261), Kumho P&B. The same may apply hereinafter.) was added to the flask, and 8 ml of allyl bromide (Sigma Aldrich. The same may apply hereinafter.) was added thereto drop by drop, followed by stirring at room temperature for 20 hours for performing reaction. After completing the reaction, 300 ml of water was added, and the reaction product was extracted with ethyl acetate. Then, the extract was washed with brine, dried with $MgSO_4$, and filtered using a filter, and solvents were removed using an evaporator to obtain an allylated epoxy compound. The reaction scheme is as follows.

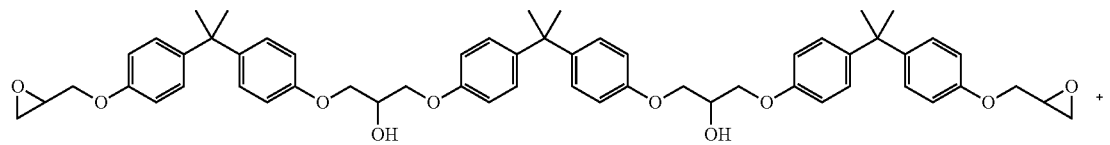

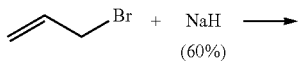

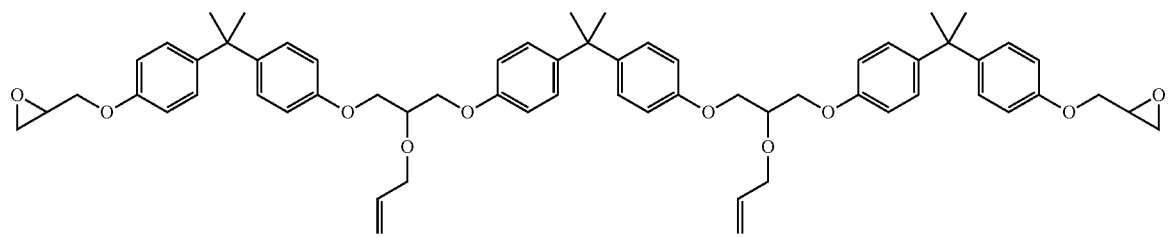

¹H NMR (400 MHz, CDCl₃): δ1.62 (s, 27H), 2.72-2.74 (m, 2H), 2.87-2.89 (m, 2H), 3.31-3.34 (m, 2H), 3.92 (dd, J=4.8 Hz, 2H), 4.06-4.19 (m, 10H), 4.23-4.24 (m, 2H), 5.18 (dd, J=0.8 Hz, 2H), 5.30 (dd, J=1.2 Hz, 2H), 5.90-5.97 (m, 2H), 6.80-6.82 (m, 12H), 7.11-7.14 (m, 12H).

Step (2)—Hydrosilylation 16 g of the allylated epoxy compound obtained in the above step (1), 6 ml of triethoxysilane (TCI, The same may apply hereinafter.), 70 mg of platinum oxide, and 40 ml of toluene were added to a 100 ml flask at room temperature, followed by charging with argon and stirring at 85° C. for 24 hours. Then, the reaction product was filtered using a celite filter, and solvents were removed using an evaporator to obtain an epoxy compound having an alkoxysilyl group (DGEBA-HS). The reaction scheme is as follows.

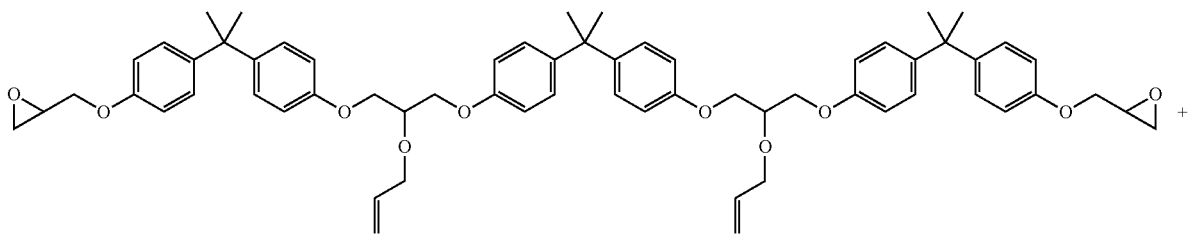

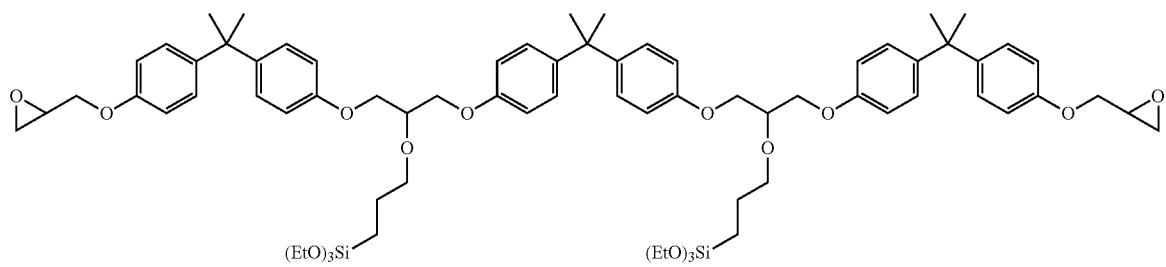

$^1$H NMR (400 MHz, CDCl$_3$): δ0.64-0.68 (m, 4H), 1.19-1.30 (m, 18H), 1.55-1.74 (m, 22H), 2.73 (q, J=2.4 Hz, 2H), 2.88 (t, J=4.4 Hz, 2H), 3.31-3.35 (m, 2H), 3.65 (t, J=7.0 Hz, 4H), 3.79-3.85 (m, 12H), 3.92-4.00 (m, 6H), 4.06-4.19 (m, 8H), 6.80-6.82 (m, 12H), 7.10-7.14 (m, 12H).

Synthetic Example 2

Step (1)—Allylation of Hydroxyl Group 3 g of sodium hydride (60 wt %, dispersed in mineral oil) and 200 ml of DMF were added to a 1 L flask, followed by stirring and mixing at room temperature. Then, 35.0 g of an epoxy compound (DGEBA (EEW261)) was added to the flask, and 9 ml of 5-bromopentene was added thereto drop by drop, followed by stirring at room temperature for 24 hours for performing reaction. After completing the reaction, 300 ml of water was added, and the reaction product was extracted with ethyl acetate. Then, the extract was washed with brine, dried with MgSO$_4$, and filtered using a filter, and solvents were removed using an evaporator to obtain an allylated epoxy compound. The reaction scheme is as follows.

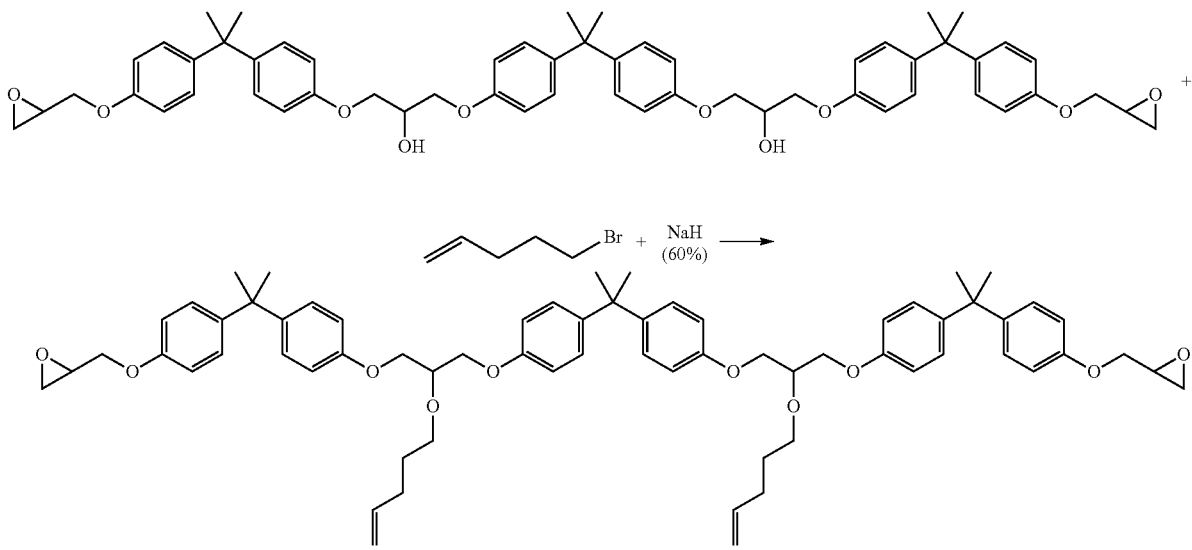

$^1$H NMR (400 MHz, CDCl$_3$): δ1.25 (t, J=3.2, 4H), 1.62 (s, 27H), 1.68-1.74 (m, 2H), 2.08-2.15 (m, 2H), 2.72-2.74 (m, 2H), 2.87-2.89 (m, 2H), 3.31-3.34 (m, 2H), 3.92 (dd, J=4.8 Hz, 2H), 4.06-4.19 (m, 10H), 4.23-4.24 (m, 2H), 5.18 (dd, J=0.8 Hz, 2H), 5.30 (dd, J=1.2 Hz, 2H), 5.90-5.97 (m, 2H), 6.80-6.82 (m, 12H), 7.11-7.14 (m, 12H).

Step (2)—Hydrosilylation 32.0 g of the allylated epoxy compound obtained in the above step (1), 12 ml of triethoxysilane, 150 mg of platinum oxide, and 100 ml of toluene were added to a 250 ml flask at room temperature, followed by charging with argon and stirring at 85° C. for 24 hours. Then, the reaction product was filtered using a celite filter, and solvents were removed using an evaporator to obtain an epoxy compound having an alkoxysilyl group (DGEBA-p-HS). The reaction scheme is as follows.

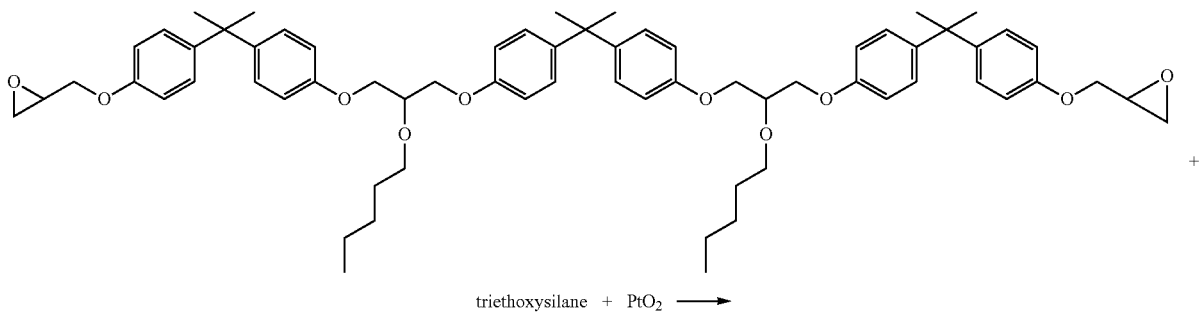

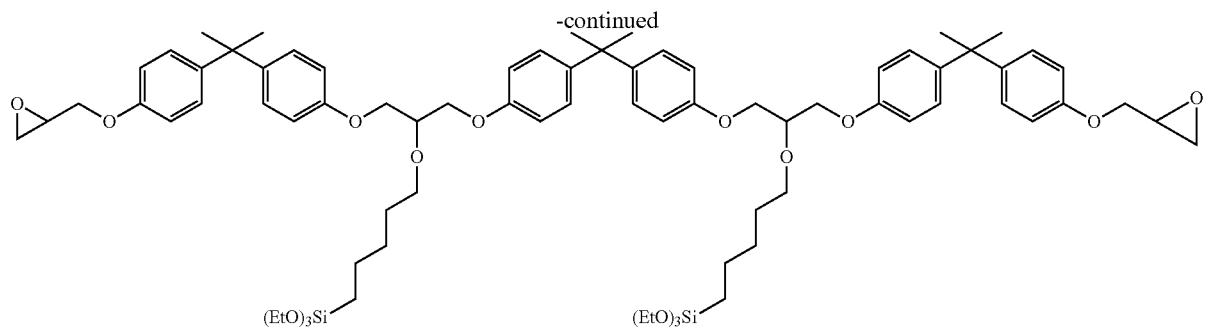

-continued

¹H NMR (400 MHz, CDCl₃): δ0.64-0.68 (m, 4H), 1.19-1.30 (m, 18H), 1.34-1.42 (m, 4H), 1.55-1.74 (m, 26H), 2.73 (q, J=2.4 Hz, 2H), 2.88 (t, J=4.4 Hz, 2H), 3.31-3.35 (m, 2H), 3.65 (t, J=7.0 Hz, 4H), 3.79-3.85 (m, 12H), 3.92-4.00 (m, 6H), 4.06-4.19 (m, 8H), 6.80-6.82 (m, 12H), 7.10-7.14 (m, 12H).

Synthetic Example 3

Step (1)—Allylation of Hydroxyl Group 5.3 g of sodium hydride (60 wt %, dispersed in mineral oil) and 300 ml of DMF were added to a 1 L flask, followed by stirring and mixing at room temperature. Then, 40.0 g of an epoxy compound (NET-676) in the following reaction scheme was added to the flask, and 14 ml of allyl bromide was added thereto drop by drop, followed by stirring at room temperature for 24 hours for performing reaction. After completing the reaction, 300 ml of water was added, followed by stirring for 5 minutes, and the reaction product was extracted with ethyl acetate. Then, the extract was washed with brine, dried with MgSO₄, and filtered using a filter, and solvents were removed using an evaporator to obtain an allylated epoxy compound. The reaction scheme is as follows.

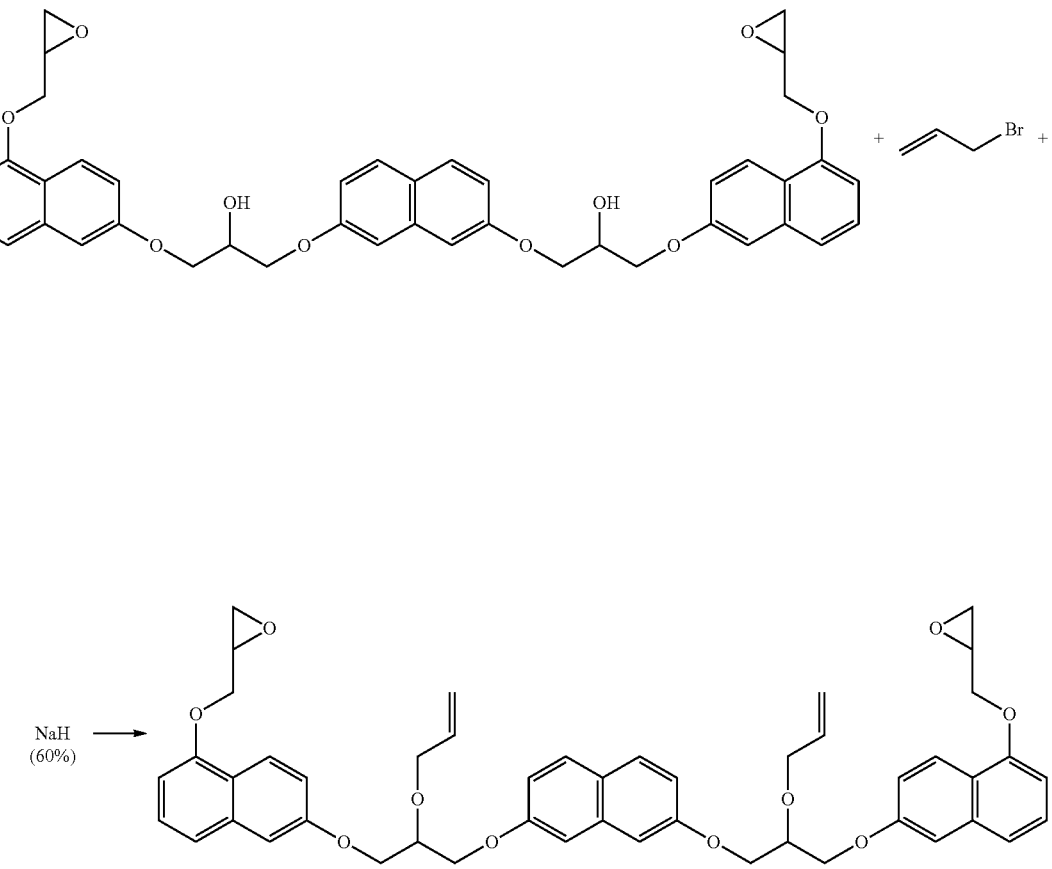

¹H NMR (400 MHz, CDCl₃): δ2.79-2.85 (m, 2H), 2.93-2.97 (m, 2H), 3.39-3.47 (m, 2H), 4.11-4.14 (m, 2H), 4.24-4.40 (m, 16H), 5.30-5.40 (m, 4H), 5.96-6.05 (m, 2H), 7.03-7.10 (m, 5H), 7.13-7.19 (m, 3H), 7.31-7.36 (m, 4H), 7.66 (d, J=7.2 Hz, 2H), 8.17-8.21 (m, 2H).

Step (2)—Hydrosilylation 20.0 g of the allylated epoxy compound obtained in the above step (1), 10 ml of triethoxysilane, 100 mg of platinum oxide, and 60 ml of toluene were added to a 100 ml flask at room temperature, followed by charging with argon and stirring at 85° C. for 24 hours. Then, the reaction product was filtered using a celite filter, and solvents were removed using an evaporator to obtain an epoxy compound having an alkoxysilyl group (NET-HS). The reaction scheme is as follows.

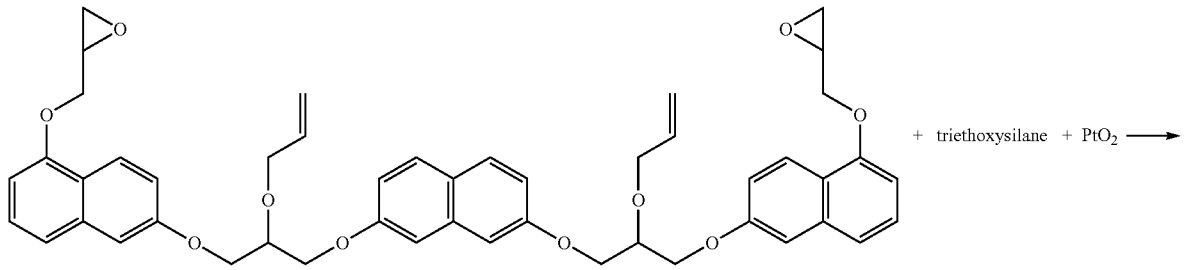

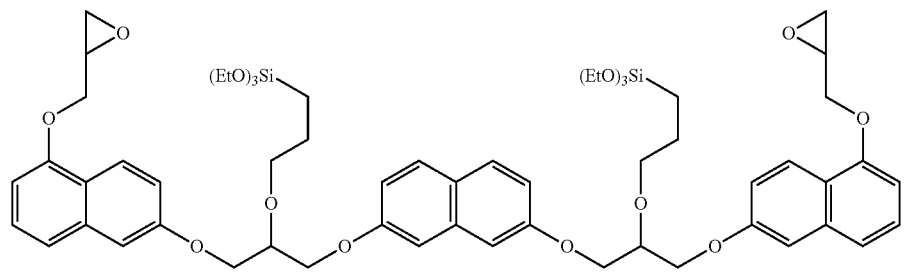

¹H NMR (400 MHz, CDCl₃): δ0.68-0.72 (m, 4H), 1.18-1.26 (m, 18H), 1.75-1.81 (m, 4H), 2.81 (dq, J=2.4 Hz, 2H), 2.94 (dt, J=4.8 Hz, 2H), 3.40-3.47 (m, 2H), 3.69-3.89 (m, 14H), 4.05-4.18 (m, 4H), 4.23-4.56 (m, 12H), 7.03-7.18 (m, 8H), 7.29-7.33 (m, 4H), 7.65 (d, J=8.8 Hz, 2H), 8.18-8.20 (m, 2H).

Synthetic Example 4

48 g of DGEBA (EEW: 261, Kumho P&B), 32 ml of triethylamine, 50 ml of 3-(triethoxysilyl)propyl isocyanate, and 300 ml of methylene chloride were added to a 500 ml flask at room temperature, followed by refluxing for 1 hour. Then, solvents were removed using an evaporator to obtain an epoxy compound having an alkoxysilyl group (DGEBA-ISO). The reaction scheme is as follows.

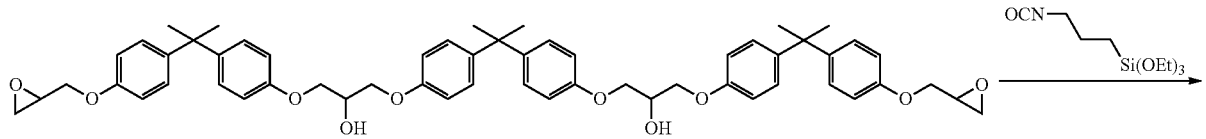

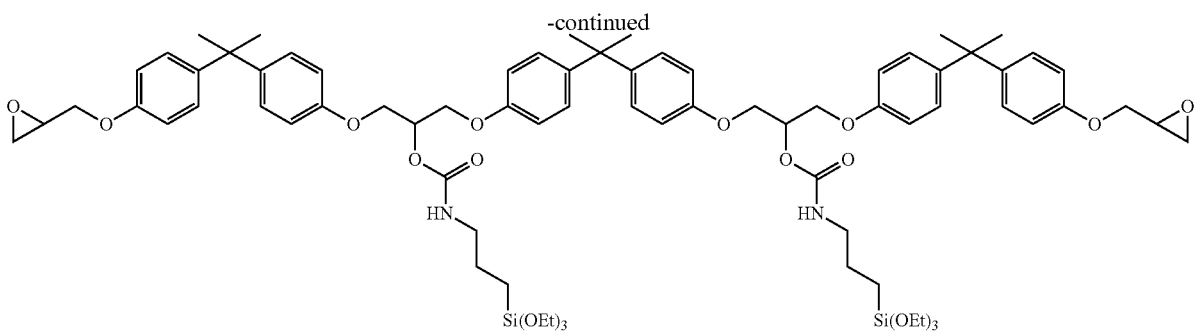

¹H NMR (500 MHz, CDCl₃): δ=0.63-0.65 (m, 4H), 1.13-1.24 (m, 18H), 1.61-1.67 (m, 22H), 2.75 (q, J=2.5 Hz, 2H), 2.91 (t, J=4.5 Hz, 2H), 3.18-3.21 (m, 2H), 3.34-3.36 (m, 4H), 3.70-3.84 (m, 12H), 3.92-3.95 (m, 4H), 4.12-4.25 (m, 8H), 5.33-5.39 (m, 2H), 6.81-6.82 (m, 12H), 7.11-7.13 (m, 12H), 8.59 (br, 2H).

Synthetic Example 5

20.00 g of a naphthalene trimer epoxy compound (NET-676) in the following reaction scheme as an epoxy compound, 20 ml of triethylamine, 30 ml of 3-(triethoxysilyl)propyl isocyanate, and 200 ml of methylene chloride were added to a 500 ml flask at room temperature, followed by refluxing for 1 hour. Then, solvents were removed using an evaporator to obtain a compound having an alkoxysilyl group (NET-ISO). The reaction scheme is as follows.

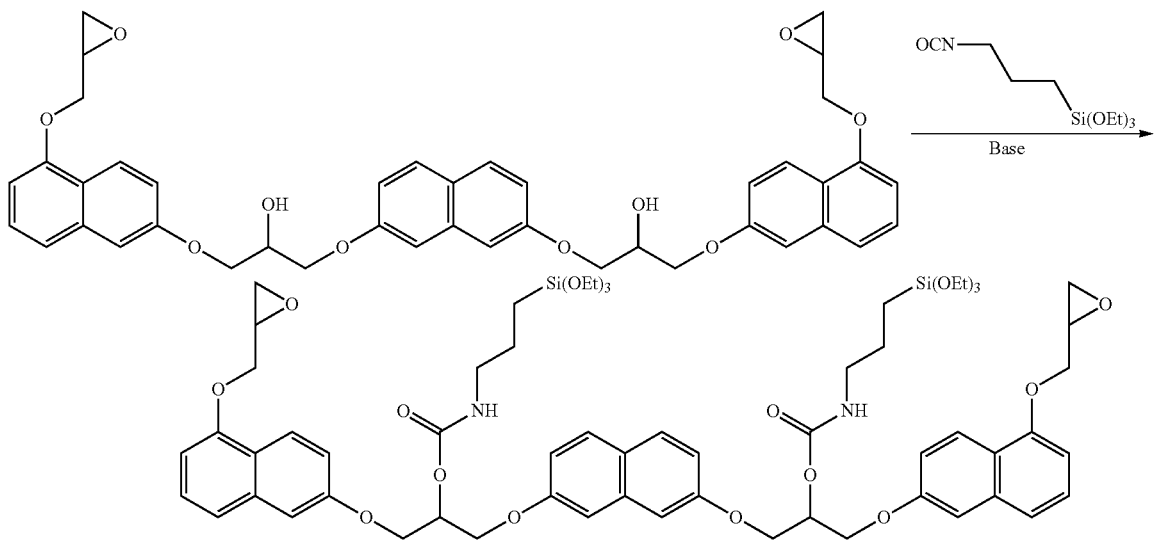

¹H NMR (400 MHz, CDCl₃): δ=0.59-0.63 (m, 4H), 1.18-1.26 (m, 18H), 1.57-1.64 (m, 4H), 2.81 (dq, J=2.4 Hz, 2H), 2.94 (dt, J=4.8 Hz, 2H), 3.16 (q, J=6.4 Hz, 4H), 3.39-3.48 (m, 2H), 3.69-3.89 (m, 14H), 4.23-4.56 (m, 12H), 5.15 (t, J=6.0 Hz, 2H), 7.03-7.18 (m, 8H), 7.29-7.33 (m, 4H), 7.65 (d, J=8.8 Hz, 2H), 8.18-8.20 (m, 2H).

Synthetic Example 6

10.00 g of an epoxy compound (NED-66) in the following reaction scheme, 7.13 ml of triethylamine, 10.14 ml of 3-(triethoxysilyl)propyl isocyanate, and 100 ml of methylene chloride were added to a 250 ml flask at room temperature, followed by refluxing for 1 hour. Then, solvents were removed using an evaporator to obtain a compound having an alkoxysilyl group (NED-ISO). The reaction scheme is as follows.

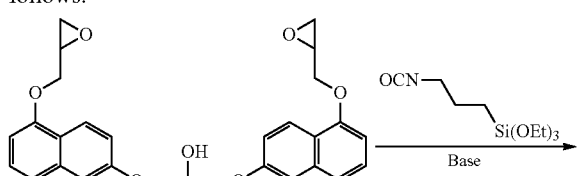

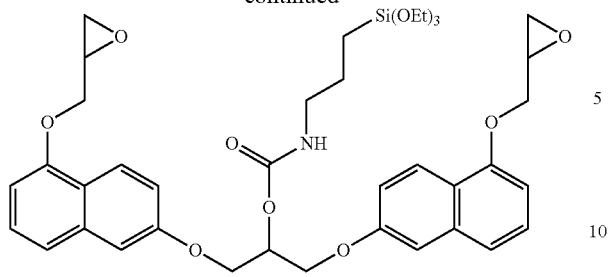

$^1$H NMR (500 MHz, CDCl$_3$): δ=0.59-0.63 (m, 2H), 1.18-1.32 (m, 9H), 1.57-1.64 (m, 2H), 2.80-2.85 (m, 2H), 2.93-2.97 (m, 2H), 3.16 (q, J=6.4 Hz, 2H), 3.41-3.49 (m, 2H), 3.73-3.87 (m, 8H), 4.25-4.42 (m, 7H), 5.15 (t, J=6.0 Hz, 1H), 6.66-6.76 (m, 2H), 7.09 (d, J=2.0 Hz, 1H), 7.13-7.19 (m, 3H), 7.30-7.36 (m, 4H), 8.18-8.21 (m, 2H).

Synthetic Example 7

10.00 g of an epoxy compound in the following reaction scheme, 5.34 ml of triethylamine, 8 ml of 3-(triethoxysilyl)propyl isocyanate, and 100 ml of methylene chloride were added to a 250 ml flask at room temperature, followed by refluxing for 1 hour. Then, solvents were removed using an evaporator to obtain a compound having an alkoxysilyl group (Biph-ISO). The reaction scheme is as follows.

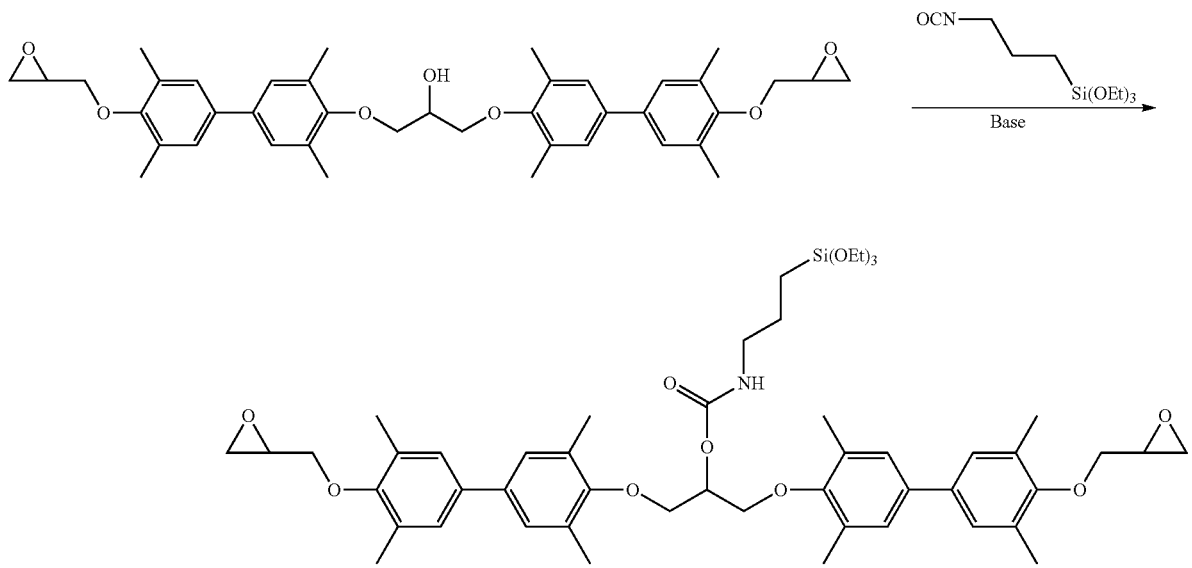

$^1$H NMR (500 MHz, CDCl$_3$): δ=0.59-0.63 (m, 2H), 1.18-1.32 (m, 9H), 1.57-1.64 (m, 2H), 2.34 (S, 24H), 2.73 (dd, J=5.0 Hz, 2H), 2.91 (dd, J=4.8 Hz, 2H), 3.16 (q, J=6.4 Hz, 2H), 3.37-3.41 (m, 2H), 3.73-3.87 (m, 8H), 4.07 (dd, J=3.2 Hz, 2H), 4.25-4.42 (m, 5H), 5.15 (t, J=6.0 Hz, 1H), 7.18 (s, 8H).

Synthetic Example 8

Step (1)—Allylation of Hydroxyl Group 0.92 g of sodium hydride (60 wt %, dispersed in mineral oil) and 100 ml of DMF were added to a 500 ml flask, followed by stirring and mixing at room temperature. Then, 10.0 g of an epoxy compound and 3.71 g of allyl bromide were added thereto drop by drop, followed by stirring at room temperature for 24 hours for performing reaction. After completing the reaction, 200 ml of water was added, followed by stirring for 5 minutes, and the reaction product was extracted with ethyl acetate. Then, the extract was washed with brine, dried with MgSO$_4$, and filtered using a filter, and solvents were removed using an evaporator to obtain an allylated epoxy compound. The reaction scheme is as follows.

$^1$H NMR (500 MHz, CDCl$_3$): δ=2.34 (S, 24H), 2.73 (dd, J=5.0 Hz, 2H), 2.91 (dd, J=4.8 Hz, 2H), 3.37-3.41 (m, 2H), 3.73-3.87 (m, 2H), 4.07 (dd, J=3.2 Hz, 2H), 4.24-4.42 (m, 7H), 5.30-5.40 (m, 2H), 5.96-6.05 (m, 1H), 7.18 (s, 8H).

Step (2)—Hydrosilylation

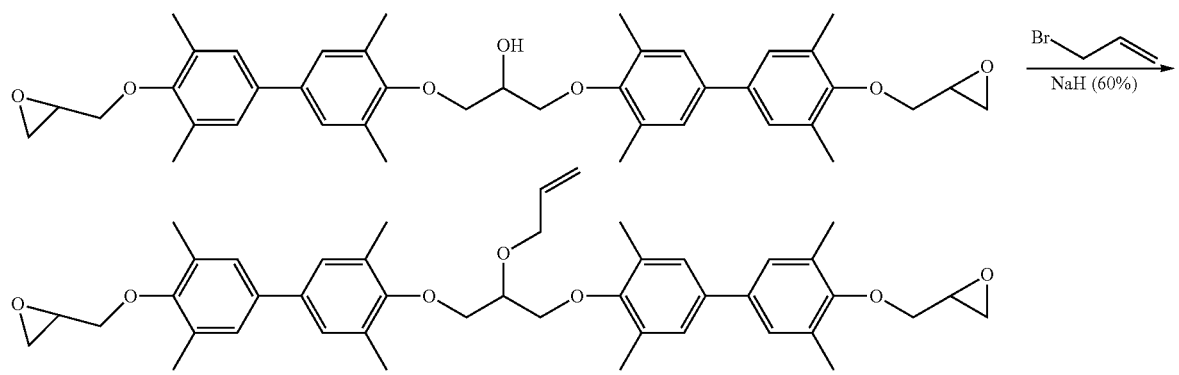

10.0 g of the allylated epoxy compound obtained in the above step (1), 2.84 g of triethoxysilane, 0.07 g of platinum oxide, and 60 ml of toluene were added to a 100 ml flask at room temperature, followed by charging with argon and stirring at 85° C. for 24 hours. Then, the reaction product was filtered using a celite filter, and solvents were removed using an evaporator to obtain an epoxy compound having an alkoxysilyl group (Biph-HS). The reaction scheme is as follows.

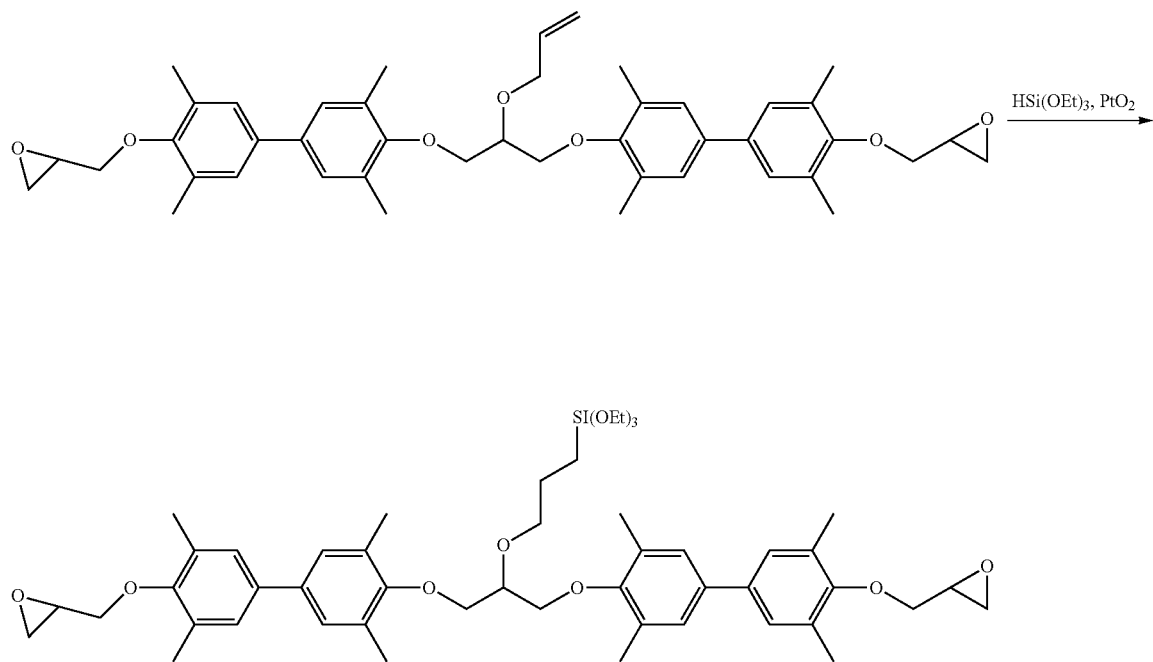

$^1$H NMR (500 MHz, CDCl$_3$): δ=0.68-0.72 (m, 2H), 1.18-1.26 (m, 9H), 1.75-1.81 (m, 2H), 2.34 (S, 24H), 2.73 (dd, J=5.0 Hz, 2H), 2.91 (dd, J=4.8 Hz, 2H), 3.37-3.41 (m, 2H), 3.65 (t, J=7.0 Hz, 2H), 3.69-3.87 (m, 8H), 4.07 (dd, J=3.2 Hz, 2H), 4.24-4.42 (m, 5H), 7.18 (s, 8H).

Expected Synthetic Example 9

Step (1)—Allylation of Hydroxyl Group 0.81 g of sodium hydride (60 wt %, dispersed in mineral oil) and 100 ml of DMF are added to a 250 ml flask, followed by stirring and mixing at room temperature. Then, 10.0 g of a binaphthalene epoxy compound and 3.27 g of allyl bromide are added thereto drop by drop in the flask, followed by stirring at room temperature for 24 hours for performing reaction. After completing the reaction, 200 ml of water is added thereto, followed by stirring for 5 minutes, and the reaction product is extracted with ethyl acetate. Then, the extract is washed with brine, dried with MgSO$_4$, and filtered using a filter, and solvents are removed using an evaporator to obtain an allylated epoxy compound. The reaction scheme is as follows.

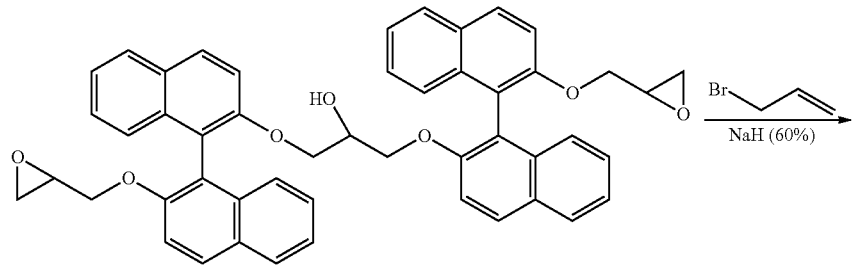

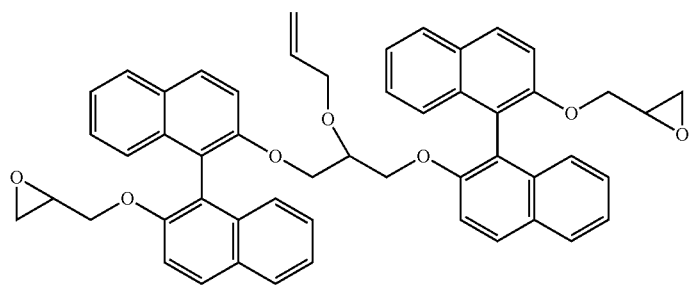

Step (2)—Hydrosilylation 10.0 g of the allylated epoxy compound obtained in the above step (1), 2.52 g of triethoxysilane, 0.06 g of platinum oxide, and 60 ml of toluene are added to a 100 ml flask at room temperature, followed by charging with argon and stirring at 85° C. for 24 hours. Then, the reaction product is filtered using a celite filter, and solvents are removed using an evaporator to obtain an epoxy compound having an alkoxysilyl group. The reaction scheme is as follows.

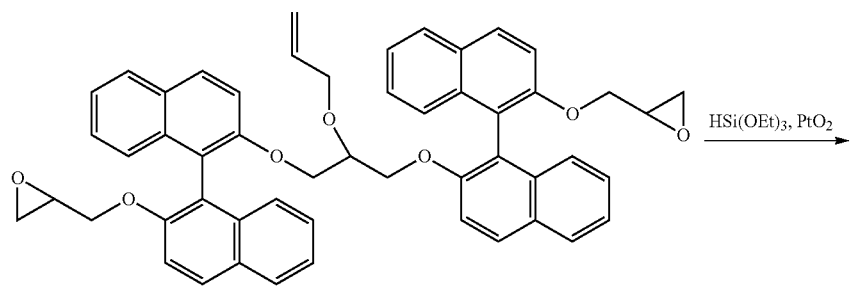

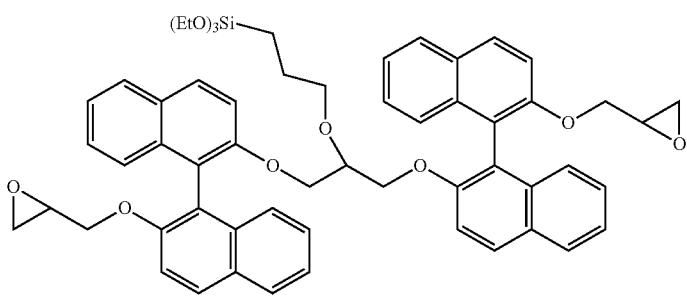

Expected Synthetic Example 10

10.00 g of a binaphthalene epoxy compound, 2.73 g of triethylamine, 3.34 g of 3-(triethoxysilyl)propyl isocyanate, and 100 ml of methylene chloride are added to a 250 ml flask at room temperature, followed by refluxing for 1 hour. Solvents are removed by using an evaporator to obtain a compound having an alkoxysilyl group. The reaction scheme is as follows.

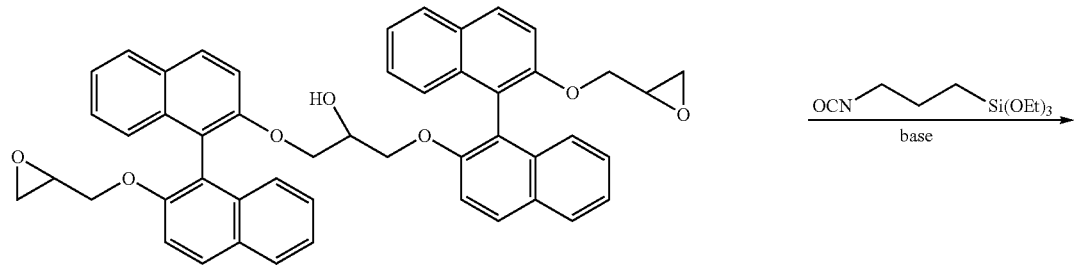

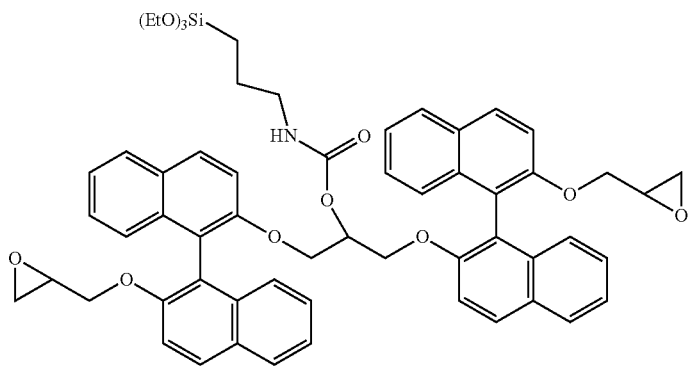

Expected Synthetic Example 11

Step (1)—Allylation of Hydroxyl Group 0.69 g of sodium hydride (60 wt %, dispersed in mineral oil) and 100 ml of DMF are added to a 250 ml flask, followed by stirring and mixing at room temperature. Then, 10.0 g of an epoxy compound, 1,3-bis(4-(9-(4-(oxirane-2-ylmethoxy)phenyl)-9H-fluorene-9-yl)phenoxy)propane-2-ol (Sigma Aldrich), and 2.78 g of allyl bromide are added thereto drop by drop, followed by stirring at room temperature for 24 hours for performing reaction. After completing the reaction, 200 ml of water is added, followed by stirring for 5 minutes, and the reaction product is extracted with ethyl acetate. Then, the extract is washed with brine, dried with MgSO$_4$, and filtered using a filter, and solvents are removed using an evaporator to obtain an allylated epoxy compound. The reaction scheme is as follows.

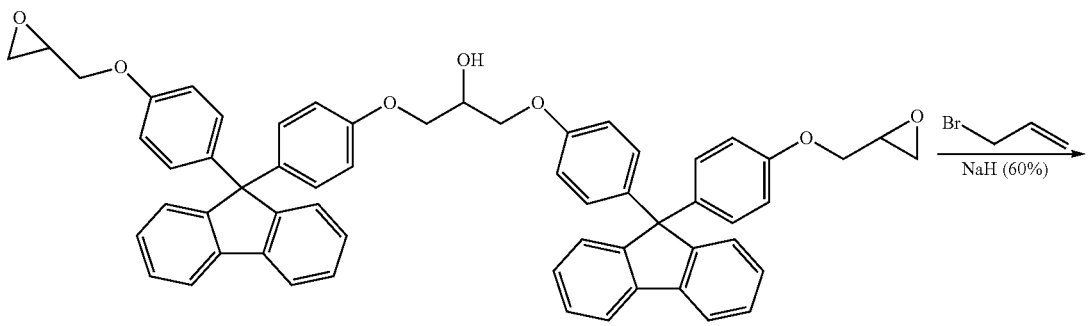

-continued

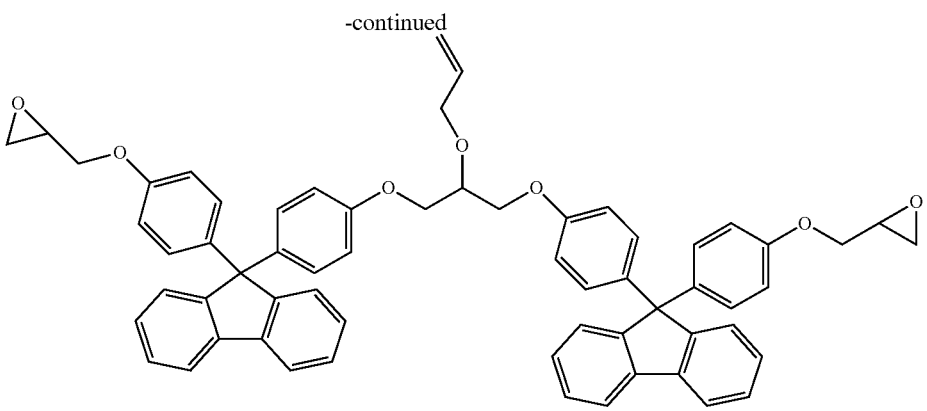

Step (2)—Hydrosilylation 10.0 g of the allylated epoxy compound obtained in the above step (1), 2.17 g of triethoxysilane, 0.05 g of platinum oxide, and 60 ml of toluene are added to a 100 ml flask at room temperature, followed by charging with argon and stirring at 85° C. for 24 hours. Then, the reaction product is filtered using a celite filter, and solvents are removed using an evaporator to obtain an epoxy compound having an alkoxysilyl group. The reaction scheme is as follows.

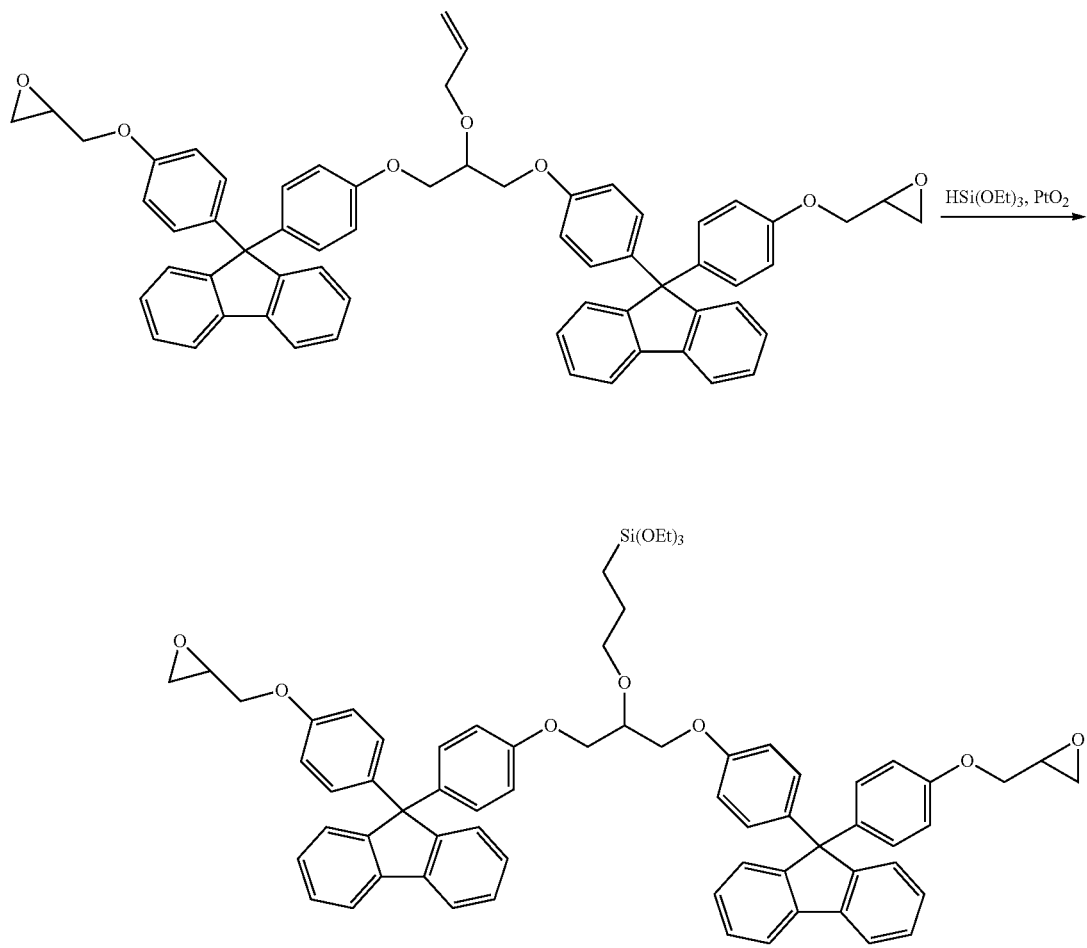

Expected Synthetic Example 12

10.00 g of an epoxy compound, 1,3-bis(4-(9-(4-(oxirane-2-ylmethoxy)phenyl)-9H-fluorene-9-yl)phenoxy)propane-2-ol, 2.33 g of triethylamine, 2.84 g of 3-(triethoxysilyl) propyl isocyanate, and 100 ml of methylene chloride are added to a 250 ml flask at room temperature, followed by refluxing for 1 hour. Solvents are removed by using an evaporator to obtain a compound having an alkoxysilyl group. The reaction scheme is as follows.

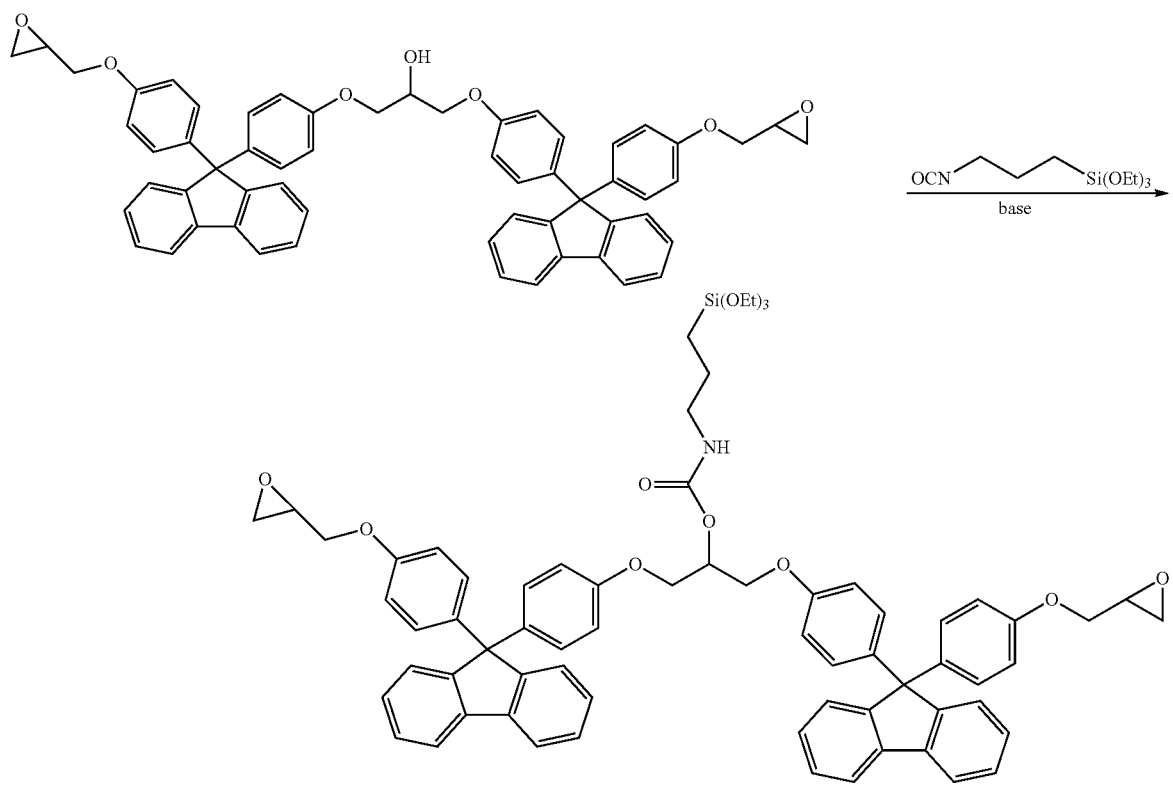

Evaluation of Physical Properties: Manufacturing of Cured Product and Evaluation of Properties 1. Manufacturing of Epoxy Glass Fiber Composite (1) Manufacturing of Heat Cured Composite A glass fiber composite including an epoxy compound was manufactured by dissolving an epoxy compound, a curing agent, and a curing catalyst in methyl ethyl ketone according to the components illustrated in the following Table 1 so that a solid content was 40 wt %, uniformly mixing to obtain a mixture, and immersing a glass fiber (glass fiber fabric by Nittobo Co., E-glass 2116) in the mixture. Then, the composite was inserted into a heated vacuum oven at 100° C. to remove solvents, and was cured in a preheated hot press to 120° C., at 120° C. for 2 hours, at 180° C. for 2 hours and at >200° C. for 2 hours to manufacture a glass fiber composite film (4 mm×16 mm×0.1 mm). While manufacturing the composite film, the resin content of the composite film was controlled according to the pressure of a press and the viscosity of a resin, and the resin content in the composite film is illustrated in the following Table 1.

When a composition for a glass fiber composite includes silica, an epoxy compound, and a silica slurry (70 wt % of solid content, 2-methoxyethanol solvent, 1 μm of silica average size) were dissolved in methyl ethyl ketone according to the components illustrated in the following Table 1 so that a solid content was 40 wt %. The mixture thus obtained was mixed in a rate of 1,500 rpm for 1 hour, and a curing agent was added, followed by further mixing for 50 minutes. Finally, a curing accelerator was added and mixed for 10 minutes to obtain an epoxy mixture. A glass fiber composite was manufactured by immersing a glass fiber (glass fiber fabric by Nittobo Co., E-glass 2116) in the epoxy mixture. Then, the same curing process was performed under the same conditions as described above to manufacture a composite film.

(2) Manufacturing of Photocurable Composite

An epoxy compound and a photo initiator, i.e., triarylsulfonium hexafluoroantimonate were dissolved in dichloromethane according to the components illustrated in the following Table 1 (Example 4, Example 16 and Comparative Example 2) so that a solid content was 70 wt %. After mixing until a homogeneous solution was obtained, a glass fiber (glass fiber fabric by Nittobo Co., E-glass 2116) was immersed in the mixture thus obtained, and solvents were removed in a vacuum oven heated to 100° C., and cooled to room temperature. The epoxy mixture was inserted between release treated glass substrates, and both sides were exposed to UV to manufacture a photocured glass fiber composite.

2. Manufacturing of Epoxy Filler Composite (Cured Product)

An epoxy compound, and a silica slurry (70 wt % of solid content, 2-methoxyethanol solvent, 1 μm of silica average size) were dissolved in methyl ethyl ketone according to the components illustrated in the following Table 2 so that a solid content was 40 wt %. The mixture thus obtained was mixed in a rate of 1,500 rpm for 1 hour, and a curing agent was added, followed by further mixing for 50 minutes. Finally, a curing catalyst was added and mixed for 10 minutes to obtain an epoxy mixture. Then, the mixture was inserted into a heated vacuum oven to 100° C. to remove solvents, and was cured in a preheated hot press to 120° C., at 120° C. for 2 hours, at 180° C. for 2 hours and at >200° C. for 2 hours to manufacture an epoxy filler (inorganic particles) composite (5 mm×5 mm×3 mm).

3. Evaluation of Heat Resistance Properties

The dimensional changes with respect to the temperature of the cured products obtained in the Examples and Comparative Examples in the following Tables 1 and 2 were evaluated by using a Thermo-mechanical analyzer and are illustrated in the following Tables. The specimens of the epoxy glass fiber composite film were manufactured in a size of 4 mm×16 mm×0.1 mm, and the specimens of the filler compositees were manufactured in a size of 5 mm×5 mm×3 mm.

TABLE 1

Epoxy glass fiber composite

| | Epoxy compound (Synthetic Example No.) | | Example 1 | Example 2 | Example 3 | Example 4 | Example 5 | Example 6 | Example 7 | Example 8 | Example 9 | Example 10 |
|---|---|---|---|---|---|---|---|---|---|---|---|---|
| Epoxy mixture component (g) | Epoxy | DGEBA-HS (1) | 5.00 | 5.00 | 2.50 | 5.00 | | | | | | |
| | | DGEBA-p-HS (2) | | | | | 5.00 | 2.50 | 5.00 | 2.50 | | |
| | | NET-HS (3) | | | | | | | | | 5.00 | 5.0 |
| | | DGEBA-ISO (4) | | | | | | | | | | |
| | | NET-ISO (5) | | | | | | | | | | |
| | | NED-ISO (6) | | | | | | | | | | |
| | | Biph-ISO (7) | | | | | | | | | | |
| | | Biph-HS (8) | | | | | | | | | | |
| | | TGIC[1] | | | 2.5 | | | 2.50 | | 2.50 | | |
| | | DGEBA[2] | | | | | | | | | | |
| | | NET 676[3] | | | | | | | | | | |
| | | NED 66[4] | | | | | | | | | | |
| | | Biphenyl epoxy[5] | | | | | | | | | | |
| | DDM[6] | | 0.8 | | 1.70 | | 1.0 | 1.76 | | | 0.50 | 0.92 |
| | HF-1M[7] | | | 1.80 | | | | | 2.04 | 3.72 | | |
| | TPP[8] | | | 0.05 | | | | | 0.05 | 0.05 | | |
| | Photo initiator[9] | | | | | 0.15 | | | | | | |
| | Naphtol[10] | | | | | | | | | | | |
| | Tin-OC[11] | | | | | | | | | | | |
| | 2E4M[12] | | | | | | | | | | | |
| | Silica | | | 0.50 | | | | | | | | |
| | Resin content (wt %) | | 38 | 37 | 38 | 48 | 36 | 38 | 38 | 38 | 39 | 35 |
| Heat resistance | CTE (ppm/° C.) | $\alpha_1$ (T < Tg) | 11.7 | 10.7 | 11.8 | 14 (photo cured) | 9.2 | 11.5 | 11.0 | 12.2 | 11.5 | 9.32 |
| | Tg (° C.) | | Tg-less | 200 | Tg-less | 155 | 200 | Tg-less | Tg-less | 180 | 150 | Tg-less |

| | Epoxy compound (Synthetic Example No.) | | Example 11 | Example 12 | Example 13 | Example 14 | Example 15 | Example 16 | Example 17 | Example 18 | Example 19 | Example 20 |
|---|---|---|---|---|---|---|---|---|---|---|---|---|
| Epoxy mixture component (g) | Epoxy | DGEBA-HS (1) | | | | | | | | | | |
| | | DGEBA-p-HS (2) | | | | | | | | | | |
| | | NET-HS (3) | | | | | | | | | | |
| | | DGEBA-ISO (4) | 2.50 | 5.00 | 5.00 | 2.50 | 2.50 | 5.00 | | | | |
| | | NET-ISO | | | | | | | 5.00 | | | |

TABLE 1-continued

Epoxy glass fiber composite

| | | | C1 | C2 | C3 | C4 | C5 | C6 | C7 | C8 | C9 | C10 |
|---|---|---|---|---|---|---|---|---|---|---|---|---|
| | | (5) NED-ISO (6) | | | | | | | | 5.00 | | |
| | | Biph-ISO (7) | | | | | | | | | 5.00 | 5.00 |
| | | Biph-HS (8) | | | | | | | | | | |
| | | TGIC(1) | 2.50 | | | 2.50 | 2.50 | | | | | |
| | | DGEBA(2) | | | | | | | | | | |
| | | NET-OH(3) | | | | | | | | | | |
| | | NED-OH(4) | | | | | | | | | | |
| | | Biphenyl epoxy(5) | | | | | | | | | | |
| | | DDM(6) | 1.60 | | | | | | 0.41 | 0.67 | 0.55 | |
| | | HF-1M(7) | | 1.53 | 1.53 | 3.46 | | | | | | 1.18 |
| | | TPP(8) | | 0.05 | 0.05 | 0.05 | | | | | | 0.05 |
| | | Photo initiator(9) | | | | | | 0.15 | | | | |
| | | Naphtol(10) | | | | | 0.52 | | | | | |
| | | Tin-OC(11) | | | | | | | | | | |
| | | 2E4M(12) | | | | | 0.05 | | | | | |
| | | Silica | | | 0.50 | | | | | | | |
| | | Resin content (wt %) | 39 | 37 | 38 | 45 | 38 | 45 | 39 | 39 | 37 | 39 |
| Heat resistance | CTE (ppm/°C.) | $\alpha_1$ (T < Tg) | 10.0 | 11.2 | 8.81 | 14.3 | 10.1 | Not photo cured | 12.8 | 11.0 | 10.8 | 9.80 |
| | Tg (°C.) | | Tg-less | Tg-less | Tg-less | Tg-less | Tg-less | 190 | 200 | Tg-less | Tg-less | |

| | | Epoxy compound (Synthetic Example No.) | Example 21 | Example 22 | Comparative Example 1 | Comparative Example 2 | Comparative Example 3 | Comparative Example 4 | Comparative Example 5 |
|---|---|---|---|---|---|---|---|---|---|
| Epoxy mixture component (g) | Epoxy | DGEBA-HS (1) | | | | | | | |
| | | DGEBA-p-HS (2) | | | | | | | |
| | | NET-HS (3) | | | | | | | |
| | | DGEBA-ISO (4) | | | | | | | |
| | | NET-ISO (5) | | | | | | | |
| | | NED-ISO (6) | | | | | | | |
| | | Biph-ISO (7) | 5.00 | | | | | | |
| | | Biph-HS (8) | | 5.00 | | | | | |
| | | TGIC(1) | | | | | | | |
| | | DGEBA(2) | | | 5.00 | 5.00 | | | |
| | | NET-OH(3) | | | | | 5.00 | | |
| | | NED-OH(4) | | | | | | 5.00 | |
| | | Biphenyl epoxy(5) | | | | | | | 5.00 |
| | | DDM(6) | | | 0.95 | | 1.2 | | |
| | | HF-1M(7) | 1.18 | 1.20 | | | | | 3.59 |
| | | TPP(8) | 0.05 | 0.05 | | | | | 0.05 |
| | | Photo initiator(9) | | | | 0.15 | | | |
| | | Naphtol(10) | | | | | | | |
| | | Tin-OC(11) | 0.20 | | | | | | |
| | | 2E4M(12) | | | | | | | |
| | | Silica | | | | | | | |
| | | Resin content (wt %) | 40 | 39 | 40 | 48 | 40 | 39 | 38 |
| Heat resistance | CTE (ppm/°C.) | $\alpha_1$ (T < Tg) | 11.0 | 10.0 | 15.3 | 17.9 (photo cured) | 14.0 | 12.8 | 14 |
| | Tg (°C.) | | Tg-less | Tg-less | 150 | 145 | 160 | 165 | 160 |

TABLE 2

| | | | \multicolumn{9}{c}{Epoxy filler composite} |
|---|---|---|---|---|---|---|---|---|---|---|---|
| | Epoxy compound (Synthetic Example No.) | | Example 23 | Example 24 | Example 25 | Example 26 | Example 27 | Example 28 | Example 29 | Example 30 | Example 31 |
| Epoxy mixture component (g) | Epoxy | DGEBA-HS (1) | 5.00 | 5.00 | 5.00 | 5.00 | | | | | |
| | | DGEBA-p-HS (2) | | | | | | | | | |
| | | NET-HS (3) | | | | | | | | | |
| | | DGEBA-ISO (4) | | | | | 5.00 | 5.00 | 5.00 | 5.00 | |
| | | NET-ISO (5) | | | | | | | | | |
| | | NED-ISO (6) | | | | | | | | | |
| | | Biph-ISO (7) | | | | | | | | | 5.00 |
| | | Biph-HS (8) | | | | | | | | | |
| | | TGIC[1] | | | | | | | | | |
| | | DGEBA[2] | | | | | | | | | |
| | | NET 676[3] | | | | | | | | | |
| | | NED 66[4] | | | | | | | | | |
| | | Biphenyl epoxy[5] | | | | | | | | | |
| | DDM | | | | | | | | | | |
| | HF-1M | | 1.82 | 1.50 | 1.50 | 1.50 | 1.83 | 1.83 | 1.83 | 1.53 | 1.18 |
| | TPP | | 0.05 | 0.05 | 0.05 | 0.05 | 0.05 | 0.05 | 0.05 | 0.05 | 0.05 |
| | Photo initiator | | | | | | | | | | |
| | Naphtol | | | | | | | | | | |
| | Tin-OC | | | | | | | | | | |
| | 2E4M | | | | | | | | | | |
| | Silica | | 2.81 | 6.55 | 15.2 | 26.2 | 2.95 | 6.88 | 16.1 | 26.3 | 24.9 |
| | Silica content (wt %) | | 30 | 50 | 70 | 80 | 30 | 50 | 70 | 80 | 80 |
| Heat resistance | CTE (ppm/°C.) | $\alpha_1$ (T < Tg) | 47.5 | 34.5 | 17.6 | 10.5 | 48.6 | 35.7 | 18.5 | 11.8 | 8.84 |
| | Tg (°C.) | | 150 | 155 | Tg-less | Tg-less | 145 | 150 | Tg-less | Tg-less | Tg-less |

| | | | \multicolumn{2}{c}{Epoxy fiber composite} |
|---|---|---|---|---|
| | Epoxy compound (Synthetic Example No.) | | Comparative Example 6 | Comparative Example 7 |
| Epoxy mixture component (g) | Epoxy | DGEBA-HS (1) | | |
| | | DGEBA-p-HS (2) | | |
| | | NET-HS (3) | | |
| | | DGEBA-ISO (4) | | |
| | | NET-ISO (5) | | |
| | | NED-ISO (6) | | |
| | | Biph-ISO (7) | | |
| | | Biph-HS (8) | | |
| | | TGIC[1] | | |
| | | DGEBA[2] | 5.00 | |
| | | NET-OH[3] | | |
| | | NED-OH[4] | | |
| | | Biphenyl epoxy[5] | | 5.00 |
| | DDM[6] | | | |
| | HF-1M[7] | | 2.05 | 2.77 |
| | TPP[8] | | 0.05 | 0.05 |
| | Photo initiator[9] | | | |
| | Naphtol[10] | | | |
| | Tin-OC[11] | | | |
| | 2E4M[12] | | | |
| | Silica | | 28.4 | 31.3 |
| | Silica content (wt %) | | 80 | 80 |
| Heat resistance | CTE (ppm/°C.) | $\alpha_1$ (T < Tg) | 15.9 | 19.5 |
| | Tg (°C.) | | 100 | 120 |

[1]TGIC: Triglycidyl ether of isocyanurate (Aldrich)
[2]DGEBA: Diglycidyl ether of bisphenol A (Aldrich)
[3]NET 676

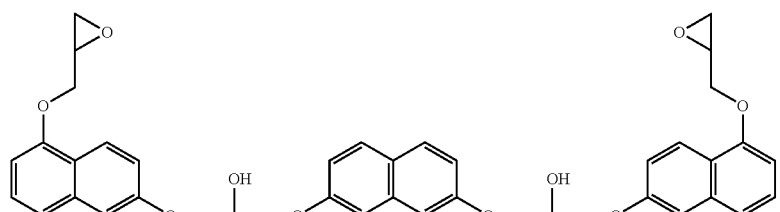

[4]NED 66

TABLE 2-continued

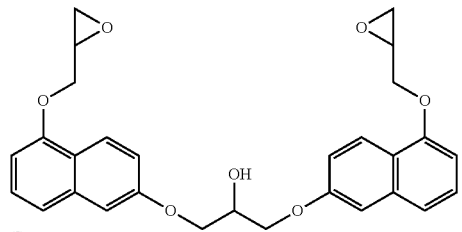 [SMILES: OC(COc1ccc2c(OCC3CO3)cccc2c1)COc1ccc2c(OCC3CO3)cccc2c1]

[5] Biphenyl epoxy resin: YX-4000H (Yuka Shell Epoxy Co.)
[6] DDM: 4,4'-diaminodiphenyl methane (Aldrich)
[7] HF-1M: Phenol novolak-based curing agent (Meiwa Plastic Industries)
[8] TPP: Triphenylphosphine (Aldrich)
[9] Photo initiator: triarylsulfonium hexafluoroantimonate salts (Aldrich)
[10] Naphtol: 1,6-dihydroxynaphthalene (Aldrich)
[11] Tin-OC: Tin(II) 2-ethylhexanoate (Aldrich)
[12] 2E4M: 2-Ethyl-4-methyl imidazole (Alrich)

As shown in the above Table 1, the CTE of the heat cured glass fiber composite of the bisphenol A-based epoxy compound modified with an alkoxysilyl group according to the present invention (Examples 1 to 3, Examples 5 to 8, and Examples 10 to 15) is 9 to 12 ppm/° C., which is relatively low when compared to CTE=15.3 ppm/° C. (E-glass) of a composite of a bisphenol A epoxy compound excluding an alkoxysilyl group (Comparative Example 1). In addition, the glass transition behavior of the heat cured glass fiber composite of the bisphenol A-based epoxy modified with the alkoxysilyl group is largely increased, and glass transition temperature is increased, or Tg-less properties are shown. Particularly, as shown in FIGS. 1 and 2, the CTE of bisphenol A-based epoxy composite modified with the alkoxysilyl group of Example 1 is very small when compared to the CTE of the composite of Comparative Example 1, and the glass transition behavior is largely improved, and Tg-less properties are shown.

The CTE of the naphthalene-based epoxy composite modified with an alkoxysilyl group according to the present invention (Examples 9, 17 and 18) is 11 to 12 ppm/° C., which is improved when compared to CTE=13 to 14 ppm/° C. of a composite of a naphthalene epoxy compound excluding an alkoxysilyl group (Comparative Examples 3 and 4). The glass transition behavior of the glass fiber composite is also improved.

In addition, the CTE of the biphenyl-based epoxy composite modified with an alkoxysilyl group according to the present invention (Examples 19 to 22) is 10 to 11 ppm/° C., which is improved when compared to CTE=14 ppm/° C. of the composite of a biphenyl-based epoxy compound excluding an alkoxysilyl group (Comparative Example 5). The glass transition behavior of the glass fiber composite is also improved.

Meanwhile, as shown in Table 2, the CTE of a composite of an epoxy compound modified with an alkoxysilyl group highly filled with inorganic materials (Examples 26, 30 and 31) is 9 to 11 ppm/° C., and very good CTE properties and Tg-less properties are obtained. On the contrary, an epoxy composite excluding an alkoxysilyl group, however highly filled with inorganic particles (Comparative Examples 6 and 7) has high CTE of 16 to 20 ppm/° C. and low glass transition temperature of 100 to 120° C.

Good CTE and glass transition temperature properties of the epoxy compound having an alkoxysilyl group observed through the present invention may be considered to be obtained due to the effective formation of bonds between systems of the alkoxysilyl group with a glass fiber and/or a filler and the additional chemical bonds between the alkoxysilyl groups.

In addition, the CTE of a photo cured composite including the bisphenol A-based epoxy compound having an alkoxysilyl group synthesized by the hydrosilylation according to Example 4 of the present invention is low when compared to the CTE of the photo cured composite of Comparative Example 2, and the glass transition temperature thereof is increased by about 10° C. From the results, the thermal expansion properties of the composite of Example 4 manufactured by photo curing are very good when compared to the composite of Comparative Example 2.

When composites are formed by heat curing an epoxy compound having an alkoxysilyl group prepared by hydrosilylation (Synthetic Example 1) and an epoxy compound having an alkoxysilyl group prepared via a carbamate connection (Synthetic Example 5), the glass transition behavior thereof are similar, however photo curing properties thereof differ greatly as shown in Examples 1 to 4 and Examples 10 to 15. That is, as shown in Example 4, the epoxy compound having an alkoxysilyl group prepared by the hydrosilylation (Synthetic Example 1) undergoes photo curing reaction very well. However, the epoxy compound having an alkoxysilyl group prepared via the carbamate connection (Synthetic Example 5) does not undergo photocuring reaction well due to N atoms included therein as shown in Example 16.

3. Evaluation of Flame Retardant Properties

Strips of the compositees according to Example 1 and Comparative Example 1 in the above Table 1 were ignited, and photographic images of the burned strips are illustrated in FIG. 3. As illustrated in FIG. 3, the strip of the composite of the epoxy compound according to Example 1 of the present invention was extinguished naturally within 1 to 2 seconds. However, the strip of the composite not including an alkoxysilyl group according to Comparative Example 1 was completely burned. Thus, it would be known that the alkoxysilylated epoxy compound according to the present invention has good flame retardant properties.

While the present invention has been shown and described in connection with the exemplary embodiments, it will be apparent to those skilled in the art that modifications and variations can be made without departing from the spirit and scope of the invention as defined by the appended claims.

The invention claimed is:

1. An epoxy composition comprising an epoxy compound having an alkoxysilyl group of the following Formula 1:

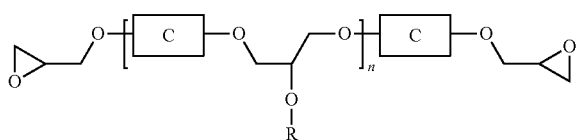

in Formula 1, a core unit C is independently selected from structures of the following Formulae 2-1 to 2-5, and each core unit C of a plurality of the core units C present in the above Formula 1 may be the same or different,

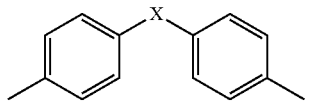 [Formula 2-1]

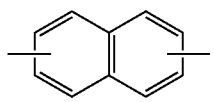 [Formula 2-2]

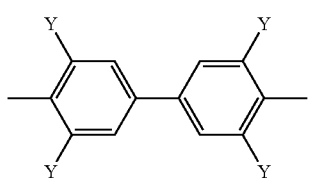 [Formula 2-3]

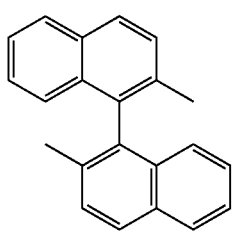 [Formula 2-4]

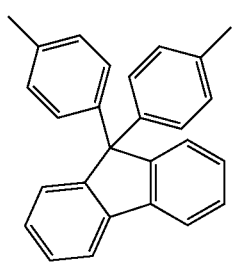 [Formula 2-5]

in Formula 2-1, X is —$CH_2$—, —$C(CH_3)_2$—, —$C(CF_3)_2$—, —S— or —$SO_2$—, in Formula 2-3, Y is independently selected from the group consisting of H and an alkyl group of C1 to C5, n is an integer from 1 to 2, in the case that n is 1, R has a structure of the following Formula 3a or 3b, and in the case that n is 2, at least one R of a plurality of R has a structure of the following Formula 3a or 3b, and the remainder thereof are hydrogen atoms,

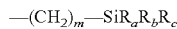 [Formula 3a]

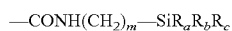 [Formula 3b]

in Formulae 3a and 3b, at least one of $R_a$ to $R_c$ is an alkoxy group having 1 to 5 carbon atoms, and the remainder thereof are alkyl groups having 1 to 10 carbon atoms, the alkoxy group and the alkyl group may be a linear chain or a branched chain alkoxy group or alkyl group, and m is an integer from 3 to 10, at least one kind of filler selected from the group consisting of an inorganic particle and a fiber;

a curing agent for the epoxy compound, the curing agent being selected from a group consisting of a phenol-based curing agent in an amount of from 0.5 to 1.5 of a stoichiometric equivalent ratio of reactive functional groups of the phenol-based curing agent to epoxy groups of the epoxy compound, and an acid anhydride-based curing agent in an amount of from 0.7 to 1.5 of a stoichiometric equivalent ratio of reactive functional groups of the anhydride-based curing agent to epoxy groups of the epoxy compound; and a catalyst selected from a group consisting of an imidazole-based catalyst in an amount of 0.1 to 7.0 parts per hundred (phr) based on the epoxy compound and a phosphorous-based catalyst in an amount of 0.1 to 2.0 phr based on the epoxy compound, wherein an epoxy group in the epoxy compound having an alkoxysilyl group reacts with the curing agent of the epoxy compound, and alkoxysilyl groups in the epoxy compound react with the filler and other alkoxysilyl groups in the epoxy compound when the composition is cured.

2. The epoxy composition of claim 1, further comprising at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound.

3. The epoxy composition of claim 2, wherein the epoxy compound comprises bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolak unit, as a core structure.

4. The epoxy composition of claim 1, wherein the epoxy composition comprises 10 wt % to 100 wt % of the epoxy compound having an alkoxysilyl group and 0 wt % to 90 wt % of at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound, based on a total amount of the epoxy compound.

5. The epoxy composition of claim 1, wherein the fiber is at least one selected from the group consisting of a glass fiber selected from the group consisting of an E-glass fiber, a T-glass fiber, an S-glass fiber, an NE-glass fiber, an E-glass fiber, a H-glass fiber and quartz, and an organic fiber selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber.

6. A cured product of the epoxy composition according to claim 1.

7. A cured product of the epoxy composition according to claim 1, wherein the cured product has a coefficient of thermal expansion of 60 ppm/° C. or less.

8. The cured product of claim 7, wherein the cured product has a glass transition temperature of 100° C. or over.

9. The cured product of claim 7, wherein the cured product does not exhibit a glass transition temperature.

* * * * *